United States Patent [19]

Searfoss, III et al.

[11] Patent Number: 5,541,109
[45] Date of Patent: Jul. 30, 1996

[54] EXPRESSION CLONING OF C-SRC SH3-DOMAIN BINDING PROTEINS

[75] Inventors: George H. Searfoss, III, Birdsboro; Yuri D. Ivashchenko, Audubon; both of Pa.

[73] Assignee: Rhone-Poulenc Rorer Pharmaceuticals Inc., Collegeville, Pa.

[21] Appl. No.: 230,047

[22] Filed: Apr. 19, 1994

[51] Int. Cl.$^6$ ............................ C12N 1/20; C12N 15/63; C07H 21/04
[52] U.S. Cl. .................. 435/252.3; 536/23.5; 435/320.1
[58] Field of Search .................................. 530/326, 327, 530/328, 329; 536/23.1, 23.2, 23.5; 435/320.1, 252.3

[56] References Cited

U.S. PATENT DOCUMENTS 5,434,064  7/1995  Schlessinger et al. ............... 435/172.3

FOREIGN PATENT DOCUMENTS 4005684  8/1991  Germany.

OTHER PUBLICATIONS

Richardson, H. E. et al. (1990) "Human cDNAs encoding homologs of the small p 34$^{cdc28/cdc2}$-associated protein of *S. cerevisiae* and *S. pombe*" Genes & Develop. 4:1332–1344.
Cell 76:933–45, 1994, Yu Chen Feng, Dalgarno Brauer et al., Structural Basis for the Binding of Proline-Rich Peptides to SH3 Domains, English Original.
J. Am. Chem. Soc. 115:12591–2, 1993, Chen Lane Brauer, Tanaka Schreiber, Biased Combinatorial Libraries: Novel Ligands for the SH3 Domain of Phosphatidylinositol 3-Kinase, English Original.
Science 249:404–6, 1990, Devlin Panganiban Devlin, Random Peptide Libraries: A Source of Specific Protein Binding Molecules, English Original.
Gene 73:305–318, 1988, Parmley Smith, Antibody-selectable filamentous fd phage vectors: affinity purification of target genes, English Original.
Science 249:386–406, 1990, Scott Smith, Searching for Peptide Ligands with an Epitope Library, English Original.
Proc. Natl. Acad. Sci. USA 87:6378–6382, 1990, Cwirla Peters Barrett, Dower, Peptides on phage: A vast library of peptides for identifying ligands, English Original.

Science 259:1157–61, 1993, Ren Mayer Cicchetti, Baltimore, Identification of a Ten–Amino Acid Proline-Rich SH3 Binding Site, English Original.
Current Biology 3(7):434–43, 1993, Pawson Schlessinger, SH2 and SH3 domains, English Original.
Cell 72:945–52, 1993, Koyama Yu Dalgarno, Shin Zydowsky Schreiber, Structure of the P13K SH3 Domain and Analysis of the SH3 Family, English Original.
Science 258:1665–8, 1992, Yu Rosen Shin, Seidel–Dugan Brugge Schreiber, Solution Structure of the SH3 Domain of Src and Identification of Its Ligand–Binding Site, English Original.
Science 257:803–6, 1992, Cicchetti Mayer Thiel, Baltimore, Identification of a Protein That Binds to the SH3 Region of Abl and Is Similar to Bcr and GAP–rho, English Original.
Cell 71:359–62, 1992, Pawson Gish, SH2 and SH3 Domains: From Structure to Function, English Original.
Science 252:668–74, 1991, Koch Anderson Moran, Ellis Pawson SH2 and SH3 Domains: Elements That Control Interactions of Cytoplasmic Signaling Proteins, English Original.
J. Cell. Biol. 119(5):1287–96, 1992, Aizawa Sekine Takemura, Zhang Nangaku Hirokawa, Kinesin Family in Murine Central Nervous System, English Original.
BioTechniques 13(6):866–869, 1992, Ron Dressler, pGSTag–A Versatile Bacterial Expression Plasmid for Ezymatic Labeling of Recombinant Proteins, English Original.
Nature Genetics 4:373–80, 1993, Adams Soares Kerlavage, Fields Venter, Rapid cDNA sequencing (expressed sequence tags) from a directionally cloned human infant brain cDNA library. English Original.

*Primary Examiner*—Robert A. Wax
*Assistant Examiner*—Kawai Lau
*Attorney, Agent, or Firm*—Julie K. Smith; Rosanne Goodman; Raymond S. Parker, III

[57] ABSTRACT

This invention provides a unique SH3 binding domain core motif of the sequence RPLPXXP and cDNA clones encoding proteins which interact with the SH3 domain of c-src, as well as the amino acid sequences which mediate this binding.

Another embodiment of this invention is a method of identifying SH3-binding proteins and elucidating the sequences which mediate binding. This method may be used as an assay to select compounds which bind to this site and which inhibit or enhance the binding of the SH3 domain.

18 Claims, 14 Drawing Sheets

```
361 GGC CTG GGG TTC AGA CCG ACA GCT GCT TTC TTG AGC TGT GAG GAA GGC GAG TTC CAC
     G   L   G   F   R   P   T   A   A   F   L   S   C   E   E   G   E   F   H
421 GGC CAA CTG ACC ACC CGG ACA GAT GCG TTC ACT GCC GTG GCC ACC AAC
     G   Q   L   T   T   R   T   D   A   F   T   A   V   A   T   N
                                              *HindIII
481 AAC CAC CCA AGA TCT TGT GGC ACA CAG CAA GTT TCA GTC CCA GCT TGT GTT
     N   H   P   R   S   C   G   T   Q   Q   V   S   V   P   A   C   V
541 CAT TGG GAC ACA CTG CTG CTG CAG GCA AAG GCA GCT GAT GTC CGA AGC ACC CAC
     H   W   D   T   L   L   L   Q   A   K   A   A   D   V   R   S   T   H
601 TAC AGC AAT CTG CTG TGT GAC CTC CTG CGT GGC ATT GTG GCC ACC AAG GCT GCC
     Y   S   N   L   L   C   D   L   L   R   G   I   V   A   T   K   A   A
661 CTG CAG TAC CCA TCC CCT TCC GCT GCC CAG GAC ATG GTG GAG CAG GGT CAA GGA GCT AGG
     L   Q   Y   P   S   P   S   A   A   Q   D   M   V   E   Q   G   Q   G   A   R
721 CCA CAG CAC TCA GCA GTT CCG CGT CCT GGG CCA GCT AGC TGC TGC CTG AGA GCA GAG
     P   Q   H   S   A   V   P   R   P   G   P   A   S   C   C   L   R   A   E
```

FIG. 6B

```
761
GAC CAG GAT GTG AGG CTG GGG ATG GGC AGC GAT GCT CTG AGC CAC CCA GCG GTT TGG GGA
 D   Q   D   V   R   L   G   M   G   S   D   A   L   S   H   P   A   V   W   G
841
CAG GTA ACC CCA GCT CTG CCT TGG CCT GGT GCC TCC AAC TGT CCA GGG ATT TGT ACA TAT
 Q   V   T   P   A   L   P   W   P   G   A   S   N   C   P   G   I   C   T   Y
901
TTA TAT CAA GGC AGG ATG TGG GAT GCC TCC TCG GAG AAG CTG AGG AGC CCA GTA GGA GTG
 L   Y   Q   G   R   M   W   D   A   S   S   E   K   L   R   S   P   V   G   V
941
TAC CGT GGG CTG GGG ATC ACC AGG ATT GGT GCA CAT GGG CCC CAA ACC TCA GGG CTC CCT
 Y   R   G   L   G   I   T   R   I   G   A   H   G   P   Q   T   S   G   L   P
1021
GTG ACA GGC AAG TAC AGT GTG GTG CAC ACC TCT GCA CCA AGA AAA ACC CTA AAG AAC TAT
 V   T   G   K   Y   S   V   V   H   T   S   A   P   R   K   T   L   K   N   Y
1081
TTT TCA CTA TTG ATT TTT CCA ATC ATT TGA CTA ATA GTC TAC ATT TAA TAA AAT TTT AAA
 F   S   L   L   I   F   P   I   I
1141                                                                     1168
AAT GCA AAA AAA AAA GCT TGG GCC CTA A
```

FIG.6C

```
241
CCC CGC CTG TTT CGC CCG CCT GCC GCC GCT CCG GAT GAG GTG ATG GCA
 P   R   L   F   R   P   P   A   A   A   P   D   E   V   M   A
                 └493
289
ACG GCC AAC TTC GGC AAG ATC CAG ATC GGG ATT TAC GTG GAG ATC AAG
 T   A   N   F   G   K   I   Q   I   G   I   Y   V   E   I   K
337          -21 C T                    +1  A A
CGC AGC GAT GGC CGA ATA CAC CAA GCA ATG GCA TCT TTA AAT GAA
 R   S   D   G   R   I   H   Q   A   M   A   S   L   N   E
385              C                  T
GAT AAT GAA AGT GTA ACT GTT GAG TGG ATA GAA AAT GGA GAT ACG AAA
 D   N   E   S   V   T   V   E   W   I   E   N   G   D   T   K
433
GGC AAA GAG ATT GAC TTG GAG AGC ATC TTT TCA CTT AAC CCT GAC CTT
 G   K   E   I   D   L   E   S   I   F   S   L   N   P   D   L
481
GTA CCT GAT GAA GAT ATT GAG CCC AGT CCA GAA CTA CCT CCT CCC TCG
 V   P   D   E   D   I   E   P   S   P   E   L   P   P   P   S
529
TCA TCC TCA AAA GTT AAC AAA ATT GTA AAG AAC CGG CGG ACT GTG GCA
 S   S   S   K   V   N   K   I   V   K   N   R   R   T   V   A
577
GCT GTT AAG AAT GAC CCT CCC CCG AGA GAT AAT AGA GTG GTT GGT TCA
 A   V   K   N   D   P   P   P   R   D   N   R   V   V   G   S
```

```
625
GCA CGC GCA CGG CCT AGT CAG CTT CCT GAG CAA TCG TCT TCT GCA CAA
 A   R   A   R   P   S   Q   L   P   E   Q   S   S   S   A   Q
673
CAG AAT GGT AGC GTT TCA GAT ATA TCT CCA GTT CAA GCT GCA AAA AAG
 Q   N   G   S   V   S   D   I   S   P   V   Q   A   A   K   K
721
GAG TTT GGC CCT CCT TCA CGT AGA AAA TCC AAT TGT GTG AAA GAA GTA
 E   F   G   P   P   S   R   R   K   S   N   C   V   K   E   V
769
GAA AAA TTG CAA GAA AAA CGA GAA AGG AGA TTG CAA CAG CAA GAA
 E   K   L   Q   E   K   R   E   R   R   L   Q   Q   Q   E
817
CTT AGA GAA AAA AGA GCC CAG GAT GTT GAT GCT ACA AAT CCA AAT TAC
 L   R   E   K   R   A   Q   D   V   D   A   T   N   P   N   Y
865
GAA ATT ATG TGT ATC AGA GAC TTC AGA GGG AGC TTG GAT TAC AGA
 E   I   M   C   I   R   D   F   R   G   S   L   D   Y   R
913
CCC CTA ACA ACA GCA GAT CCT ATT GAT GAA CAT AGG ATA TGT GTT TGT
 P   L   T   T   A   D   P   I   D   E   H   R   I   C   V   C
961                                     987/624
GTA AGA AAA CGA CCA CTC AAT AAA AAA
 V   R   K   R   P   L   N   K   K
```

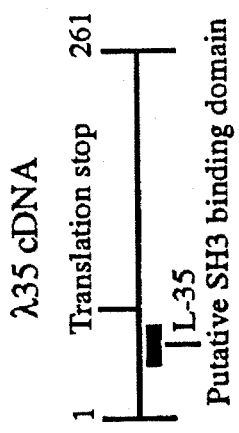

```
λ35 cDNA
         Translation stop  261
1                    |
|_____|
            |L-35
            Putative SH3 binding domain 1
AGC GAA AAA AAA CCA AAA GAA CTA AGA CAT GCC ACC CCC GCC CCG
 S   E   K   K   P   K   E   L   R   H   A   T   P   A   P
49
CCC CCA CTT CCA CCC CGC AAT GTT GCT TTT CTT GAT GGT TAA TAA
 P   P   L   P   P   R   N   V   A   F   L   D   G
97
ATA CTG TCA CGT AGC TGT GTA CAA AGA GAT GTG AAA TAC TTT CAG GCA
145
AAA ATA AAC TGT AAG TGA CTC ATG AAA GTT GGC CTT GCT GTG TGG TTG
193
TGG GTG GGG GGA TGG ACA GGG GTG GGG GGG GAT GTC TAT GCA
241                             261
GGG AGG GGG CAG GAC ACA CCT
```

FIG. 8

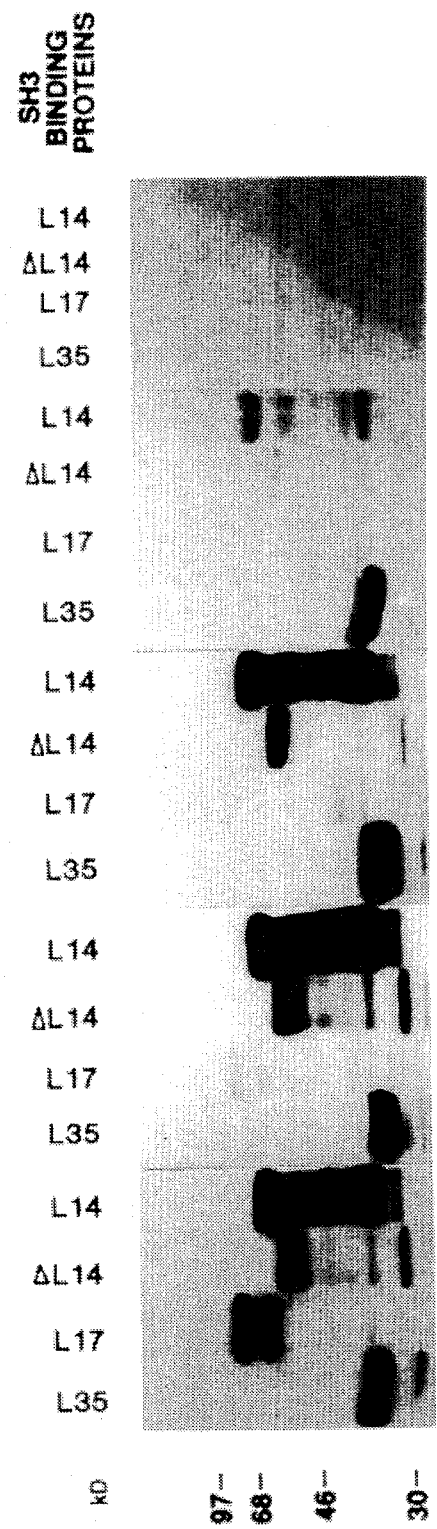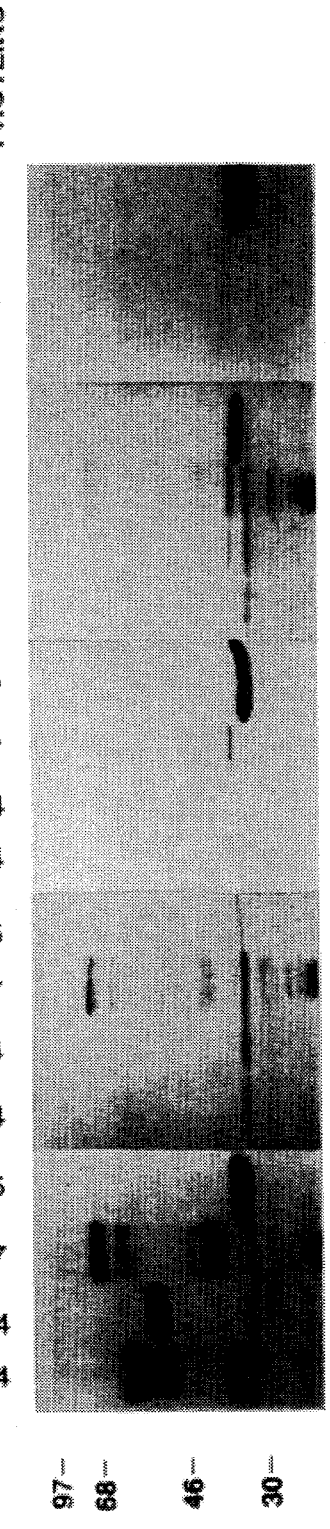

| SH3-BINDING PROTEIN | 1 | 2 | 3 | 4 | 5 | 6 | 7 | 8 | 9 | 10 | | | | | | | SH3 Ligand |
|---|---|---|---|---|---|---|---|---|---|---|---|---|---|---|---|---|---|
| Consensus | X | P | X | X | P | P | P | Ψ | X | P | | | | | | | |
| (SEQ ID NO: 1) 3BP-1 | | A | P | T | M | P | P | P | L | P | P | V | P | P | Q | P | A R cAbl, cSrc |
| (SEQ ID NO: 10) 3BP-2 | | F | P | A | Y | P | P | P | V | P | | | | | | | " |
| (SEQ ID NO: 11) Formin | | A | P | P | T | P | P | P | L | P | | | | | | | " |
| (SEQ ID NO: 12) mAChR | | P | P | A | L | P | P | P | L | P | | | | | | | " |
| (SEQ ID NO: 13) AFAP-110(76-85) | | P | P | P | D | N | G | P | P | L | P | | | | | | cSrc |
| (SEQ ID NO: 14) AFAP-110(62-71) | | P | P | P | Q | M | P | L | P | E | I | P | | | | | " |
| (SEQ ID NO: 15) Murine SOS(1149-1160) | D | E | V | P | V | P | P | P | V | P | P | R | R | | | | Grb2 |
| (SEQ ID NO: 16) SH3 BP-L35 | | | T | P | A | P | P | P | L | P | P | R | N | V | | | cSrc, Grb2, PI 3K p85, PLC |
| (SEQ ID NO: 17) SH3 BP-L14-1 | | | Q | S | R | P | L | P | S | P | P | K | F | T | | | cSrc, cFyn, PI 3K p85 |
| (SEQ ID NO: 18) Dynamin(P2) | R | R | A | P | A | V | P | P | A | R | P | G | S | | | | PI 3K p85, Grb2, cSrc |
| (SEQ ID NO: 19) SH3 BP-L17-1 | A | H | P | P | A | R | P | P | V | R | P | Q | P | G | | | PI 3K p85, PLC |
| (SEQ ID NO: 20) SH3 BP-L17-2 | | | A | P | P | A | A | T | P | P | P | R | L | F | R | P P A | PI 3K p85, PLC, Ras-GAP |
| (SEQ ID NO: 21) SV40T-peptide(control) | | K | P | P | T | P | P | P | E | P | E | T | | | | | |

FIG. 10

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear (ii) MOLECULE TYPE: peptide (ix) FEATURE:
    (A) NAME/KEY: Region
    (B) LOCATION: 8
    (D) OTHER INFORMATION: /label=hydrophobic (xi) SEQUENCE DESCRIPTION: SEQ ID NO:1:

```
Xaa  Pro  Xaa  Xaa  Pro  Pro  Pro  Xaa  Xaa  Pro
 1              5                        10
```

(2) INFORMATION FOR SEQ ID NO:2:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (xi) SEQUENCE DESCRIPTION: SEQ ID NO:2:

```
Xaa  Xaa  Xaa  Pro  Pro  Xaa  Pro  Xaa  Xaa
 1              5
```

(2) INFORMATION FOR SEQ ID NO:3:

(i) SEQUENCE CHARACTERISTICS:
       (A) LENGTH: 7 amino acids
       (B) TYPE: amino acid
       (D) TOPOLOGY: linear (ii) MOLECULE TYPE: peptide (xi) SEQUENCE DESCRIPTION: SEQ ID NO:3:

```
Arg  Pro  Leu  Pro  Xaa  Xaa  Pro
 1              5
```

(2) INFORMATION FOR SEQ ID NO:4:

(i) SEQUENCE CHARACTERISTICS:
       (A) LENGTH: 1168 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION: 1..1110

(xi) SEQUENCE DESCRIPTION: SEQ ID NO:4:

```
AGC  GAG  GGA  AGC  AGC  TCC  CTG  CAC  CCA  AAC  CCC  ACT  GAT  AAA  GCC  AGT      48
Ser  Glu  Gly  Ser  Ser  Ser  Leu  His  Pro  Asn  Pro  Thr  Asp  Lys  Ala  Ser
 1              5                        10                       15

AGC  ATC  CAG  TCA  CGC  CCT  CTC  CCC  TCA  CCT  CCA  AAG  TTC  ACC  TCC  CAG      96
Ser  Ile  Gln  Ser  Arg  Pro  Leu  Pro  Ser  Pro  Pro  Lys  Phe  Thr  Ser  Gln
                 20                       25                       30

GAC  TCT  CCA  GAC  GGC  CAG  TAT  GAG  AAC  AGT  GAA  GGG  GGT  TGG  ATG  GAG     144
Asp  Ser  Pro  Asp  Gly  Gln  Tyr  Glu  Asn  Ser  Glu  Gly  Gly  Trp  Met  Glu
                35                       40                       45

GAC  TAT  GAC  TAC  GTC  CAT  CTG  CAG  GGG  AAG  GAG  GAA  TTT  GAG  AAG  ACC     192
Asp  Tyr  Asp  Tyr  Val  His  Leu  Gln  Gly  Lys  Glu  Glu  Phe  Glu  Lys  Thr
           50                       55                       60

CAG  AAG  GAG  CTG  CTA  GAA  AGG  GGT  AAC  ATC  ATG  CGG  CAG  GGA  AAG  GGC     240
Gln  Lys  Glu  Leu  Leu  Glu  Arg  Gly  Asn  Ile  Met  Arg  Gln  Gly  Lys  Gly
65                       70                       75                       80

CAA  CTG  GAG  TTG  CAG  CAG  CTG  AAA  CAG  TTT  GAG  CGA  CTG  GAG  CAG  GAG     288
```

```
Gln Leu Glu Leu Gln Gln Leu Lys Gln Phe Glu Arg Leu Glu Gln Glu
             85                  90                  95

GTG TCT CGT CCA ATA GAC CAC GAC CTG GCC AAC TGG ACA CCA GCC CAG        336
Val Ser Arg Pro Ile Asp His Asp Leu Ala Asn Trp Thr Pro Ala Gln
            100                 105                 110

CCC CTG GTG CCG GGC CGG ACA GGG GGC CTG GGG TTC AGA CCG ACA GCT        384
Pro Leu Val Pro Gly Arg Thr Gly Gly Leu Gly Phe Arg Pro Thr Ala
            115                 120                 125

GCT GCT TTC TTG AGC TGT GAG GAA GGC GAG TTC CAC GGC CAA CTG ACC        432
Ala Ala Phe Leu Ser Cys Glu Glu Gly Glu Phe His Gly Gln Leu Thr
            130                 135                 140

ACC CGG ACA GAT GCG GTG GAC GGC TTC TTC ACT GCG GTG GCC ACC AAC        480
Thr Arg Thr Asp Ala Val Asp Gly Phe Phe Thr Ala Val Ala Thr Asn
145                 150                 155                 160

AAC CAC CCA AGA TCT TGT GGC ACA CAG CAA GTT TGT ATC TCA GTC CCA        528
Asn His Pro Arg Ser Cys Gly Thr Gln Gln Val Cys Ile Ser Val Pro
            165                 170                 175

CAA GCT TGT GTT CAT TGG GAC ACA CTG TCA CGG CAG GCA AAG GCA GCT        576
Gln Ala Cys Val His Trp Asp Thr Leu Ser Arg Gln Ala Lys Ala Ala
            180                 185                 190

GAT GTC CGA AGC CAA GTG ACC CAC TAC AGC AAT CTG CTG TGT GAC CTC        624
Asp Val Arg Ser Gln Val Thr His Tyr Ser Asn Leu Leu Cys Asp Leu
            195                 200                 205

CTG CGT GGC ATT GTG GCC ACC ACC AAG GCT GCT GCC CTG CAG TAC CCA        672
Leu Arg Gly Ile Val Ala Thr Thr Lys Ala Ala Ala Leu Gln Tyr Pro
    210                 215                 220

TCC CCT TCC GCT GCC CAG GAC ATG GTG GAG CAG GGT CAA GGA GCT AGG        720
Ser Pro Ser Ala Ala Gln Asp Met Val Glu Gln Gly Gln Gly Ala Arg
225                 230                 235                 240

CCA CAG CAC TCA GCA GTT CCG CCG CGT CCT GGG CCA GCT AGC TGC TGC        768
Pro Gln His Ser Ala Val Pro Pro Arg Pro Gly Pro Ala Ser Cys Cys
                    245                 250                 255

CTG AGA GCA GAG GAC CAG GAT GTG AGG CTG GGG ATG GGC AGC GAT GCT        816
Leu Arg Ala Glu Asp Gln Asp Val Arg Leu Gly Met Gly Ser Asp Ala
            260                 265                 270

CTG AGC CAC CCA GCG GTT TGG GGA CAG GTA ACC CCA GCT CTG CCT TGG        864
Leu Ser His Pro Ala Val Trp Gly Gln Val Thr Pro Ala Leu Pro Trp
            275                 280                 285

CCT GGT GCC CTC AAC TGT CCA GGG ATT TGT ACA TAT TTA TAT CAA GGC        912
Pro Gly Ala Leu Asn Cys Pro Gly Ile Cys Thr Tyr Leu Tyr Gln Gly
            290                 295                 300

AGG ATG TGG GAT GCC TCC TCG GAG AAG CTG AGG AGC CCA GTA GGA GTG        960
Arg Met Trp Asp Ala Ser Ser Glu Lys Leu Arg Ser Pro Val Gly Val
305                 310                 315                 320

TAC CGT GGG CTG GGG ATC ACC AGG ATT GGT GCA CAT GGG CCC CAA ACC       1008
Tyr Arg Gly Leu Gly Ile Thr Arg Ile Gly Ala His Gly Pro Gln Thr
                    325                 330                 335

TCA GGG CTC CCT GTG ACA GGC AAG TAC AGT GTG GTG CAC ACC TCT GCA       1056
Ser Gly Leu Pro Val Thr Gly Lys Tyr Ser Val Val His Thr Ser Ala
            340                 345                 350

CCA AGA AAA ACC CTA AAG AAC TAT TTT TCA CTA TTG ATT TTT CCA ATC       1104
Pro Arg Lys Thr Leu Lys Asn Tyr Phe Ser Leu Leu Ile Phe Pro Ile
            355                 360                 365

ATT TGACTAATAG TCTACATTTA ATAAATTTT AAAAATGCAA AAAAAAAGC              1157
Ile
370

TTGGGCCCTA A                                                          1168

( 2 ) INFORMATION FOR SEQ ID NO:5:
```

(i) SEQUENCE CHARACTERISTICS:
  (A) LENGTH: 369 amino acids
  (B) TYPE: amino acid
  (D) TOPOLOGY: linear (ii) MOLECULE TYPE: protein (xi) SEQUENCE DESCRIPTION: SEQ ID NO:5:

```
Ser Glu Gly Ser Ser Ser Leu His Pro Asn Pro Thr Asp Lys Ala Ser
  1               5                  10                  15
Ser Ile Gln Ser Arg Pro Leu Pro Ser Pro Pro Lys Phe Thr Ser Gln
             20                  25                  30
Asp Ser Pro Asp Gly Gln Tyr Glu Asn Ser Glu Gly Gly Trp Met Glu
             35                  40                  45
Asp Tyr Asp Tyr Val His Leu Gln Gly Lys Glu Glu Phe Glu Lys Thr
         50              55                  60
Gln Lys Glu Leu Leu Glu Arg Gly Asn Ile Met Arg Gln Gly Lys Gly
 65                  70                  75                  80
Gln Leu Glu Leu Gln Gln Leu Lys Gln Phe Glu Arg Leu Glu Gln Glu
                 85                  90                  95
Val Ser Arg Pro Ile Asp His Asp Leu Ala Asn Trp Thr Pro Ala Gln
             100                 105                 110
Pro Leu Val Pro Gly Arg Thr Gly Gly Leu Gly Phe Arg Pro Thr Ala
         115                 120                 125
Ala Ala Phe Leu Ser Cys Glu Glu Gly Glu Phe His Gly Gln Leu Thr
130                 135                 140
Thr Arg Thr Asp Ala Val Asp Gly Phe Phe Thr Ala Val Ala Thr Asn
145                 150                 155                 160
Asn His Pro Arg Ser Cys Gly Thr Gln Gln Val Cys Ile Ser Val Pro
                 165                 170                 175
Gln Ala Cys Val His Trp Asp Thr Leu Ser Arg Gln Ala Lys Ala Ala
             180                 185                 190
Asp Val Arg Ser Gln Val Thr His Tyr Ser Asn Leu Leu Cys Asp Leu
         195                 200                 205
Leu Arg Gly Ile Val Ala Thr Thr Lys Ala Ala Ala Leu Gln Tyr Pro
    210                 215                 220
Ser Pro Ser Ala Ala Gln Asp Met Val Glu Gln Gly Gln Gly Ala Arg
225                 230                 235                 240
Pro Gln His Ser Ala Val Pro Pro Arg Pro Gly Pro Ala Ser Cys Cys
                 245                 250                 255
Leu Arg Ala Glu Asp Gln Asp Val Arg Leu Gly Met Gly Ser Asp Ala
             260                 265                 270
Leu Ser His Pro Ala Val Trp Gly Gln Val Thr Pro Ala Leu Pro Trp
         275                 280                 285
Pro Gly Ala Leu Asn Cys Pro Gly Ile Cys Thr Tyr Leu Tyr Gln Gly
    290                 295                 300
Arg Met Trp Asp Ala Ser Ser Glu Lys Leu Arg Ser Pro Val Gly Val
305                 310                 315                 320
Tyr Arg Gly Leu Gly Ile Thr Arg Ile Gly Ala His Gly Pro Gln Thr
                 325                 330                 335
Ser Gly Leu Pro Val Thr Gly Lys Tyr Ser Val Val His Thr Ser Ala
             340                 345                 350
Pro Arg Lys Thr Leu Lys Asn Tyr Phe Ser Leu Leu Ile Phe Pro Ile
         355                 360                 365
Ile
```

( 2 ) INFORMATION FOR SEQ ID NO:6:

( i ) SEQUENCE CHARACTERISTICS:
        ( A ) LENGTH: 987 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..987

( x i ) SEQUENCE DESCRIPTION: SEQ ID NO:6:

```
AGC GGG GCG GGC GGC GCG AGC CTC CCA CTC TTC CCC CAG CGC GCC TCA      48
Ser Gly Ala Gly Gly Ala Ser Leu Pro Leu Phe Pro Gln Arg Ala Ser
 1               5                  10                  15

CGG CTG CGG CCC TCG CTT CAC CCG GAC GCC CGC GTG CGC GCC CGC CCG      96
Arg Leu Arg Pro Ser Leu His Pro Asp Ala Arg Val Arg Ala Arg Pro
            20                  25                  30

CCC GCT CGC CCG CCC GTC CGC CCG CAG CCC GGG GCT TCA GCC CGC TCG     144
Pro Ala Arg Pro Pro Val Arg Pro Gln Pro Gly Ala Ser Ala Arg Ser
        35                  40                  45

TCC GCG TTC GCC GCG GCC CCG CTC GCG TCC ACG CTG CCT CCC GGA CCG     192
Ser Ala Phe Ala Ala Ala Pro Leu Ala Ser Thr Leu Pro Pro Gly Pro
    50                  55                  60

GCG CGG ACG CGG GCC ACC GCT GCC CCT CCC GCC GCC ACC CCG CCC CCT     240
Ala Arg Thr Arg Ala Thr Ala Ala Pro Pro Ala Ala Thr Pro Pro Pro
 65                 70                  75                  80

CCC CGC CTG TTT CGC CCG CCT GCC GCC GCT CCG GAT GAG GTG ATG GCA     288
Pro Arg Leu Phe Arg Pro Pro Ala Ala Ala Pro Asp Glu Val Met Ala
                85                  90                  95

ACG GCC AAC TTC GGC AAG ATC CAG ATC GGG ATT TAC GTG GAG ATC AAG     336
Thr Ala Asn Phe Gly Lys Ile Gln Ile Gly Ile Tyr Val Glu Ile Lys
            100                 105                 110

CGC AGC GAT GGC CGA ATA CAC CAA GCA ATG GTG GCA TCT TTA AAT GAA     384
Arg Ser Asp Gly Arg Ile His Gln Ala Met Val Ala Ser Leu Asn Glu
        115                 120                 125

GAT AAT GAA AGT GTA ACT GTT GAG TGG ATA GAA AAT GGA GAT ACG AAA     432
Asp Asn Glu Ser Val Thr Val Glu Trp Ile Glu Asn Gly Asp Thr Lys
    130                 135                 140

GGC AAA GAG ATT GAC TTG GAG AGC ATC TTT TCA CTT AAC CCT GAC CTT     480
Gly Lys Glu Ile Asp Leu Glu Ser Ile Phe Ser Leu Asn Pro Asp Leu
145                 150                 155                 160

GTA CCT GAT GAA GAT ATT GAG CCC AGT CCA GAA CTA CCT CCA CCC TCG     528
Val Pro Asp Glu Asp Ile Glu Pro Ser Pro Glu Leu Pro Pro Pro Ser
                165                 170                 175

TCA TCC TCA AAA GTT AAC AAA ATT GTA AAG AAC CGG CGG ACT GTG GCA     576
Ser Ser Ser Lys Val Asn Lys Ile Val Lys Asn Arg Arg Thr Val Ala
            180                 185                 190

GCT GTT AAG AAT GAC CCT CCC CCG AGA GAT AAT AGA GTG GTT GGT TCA     624
Ala Val Lys Asn Asp Pro Pro Pro Arg Asp Asn Arg Val Val Gly Ser
        195                 200                 205

GCA CGC GCA CGG CCT AGT CAG CTT CCT GAG CAA TCG TCT TCT GCA CAA     672
Ala Arg Ala Arg Pro Ser Gln Leu Pro Glu Gln Ser Ser Ser Ala Gln
    210                 215                 220

CAG AAT GGT AGC GTT TCA GAT ATA TCT CCA GTT CAA GCT GCA AAA AAG     720
Gln Asn Gly Ser Val Ser Asp Ile Ser Pro Val Gln Ala Ala Lys Lys
225                 230                 235                 240

GAG TTT GGC CCT CCT TCA CGT AGA AAA TCC AAT TGT GTG AAA GAA GTA     768
Glu Phe Gly Pro Pro Ser Arg Arg Lys Ser Asn Cys Val Lys Glu Val
                245                 250                 255
```

| | | | | | | | | | | | | | | | | |
|---|---|---|---|---|---|---|---|---|---|---|---|---|---|---|---|---|
| GAA | AAA | TTG | CAA | GAA | AAA | CGA | GAA | AAA | AGG | AGA | TTG | CAA | CAG | CAA | GAA | 816 |
| Glu | Lys | Leu | Gln | Glu | Lys | Arg | Glu | Lys | Arg | Arg | Leu | Gln | Gln | Gln | Glu | |
| | | | 260 | | | | | 265 | | | | | 270 | | | |
| CTT | AGA | GAA | AAA | AGA | GCC | CAG | GAT | GTT | GAT | GCT | ACA | AAT | CCA | AAT | TAC | 864 |
| Leu | Arg | Glu | Lys | Arg | Ala | Gln | Asp | Val | Asp | Ala | Thr | Asn | Pro | Asn | Tyr | |
| | | 275 | | | | | 280 | | | | | 285 | | | | |
| GAA | ATT | ATG | TGT | ATG | ATC | AGA | GAC | TTC | AGA | GGG | AGC | TTG | GAT | TAC | AGA | 912 |
| Glu | Ile | Met | Cys | Met | Ile | Arg | Asp | Phe | Arg | Gly | Ser | Leu | Asp | Tyr | Arg | |
| | 290 | | | | | 295 | | | | | 300 | | | | | |
| CCC | CTA | ACA | ACA | GCA | GAT | CCT | ATT | GAT | GAA | CAT | AGG | ATA | TGT | GTT | TGT | 960 |
| Pro | Leu | Thr | Thr | Ala | Asp | Pro | Ile | Asp | Glu | His | Arg | Ile | Cys | Val | Cys | |
| 305 | | | | | 310 | | | | | 315 | | | | | 320 | |
| GTA | AGA | AAA | CGA | CCA | CTC | AAT | AAA | AAA | | | | | | | | 987 |
| Val | Arg | Lys | Arg | Pro | Leu | Asn | Lys | Lys | | | | | | | | |
| | | | | 325 | | | | | | | | | | | | |

( 2 ) INFORMATION FOR SEQ ID NO:7:

( i ) SEQUENCE CHARACTERISTICS:
        ( A ) LENGTH: 329 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Ser | Gly | Ala | Gly | Gly | Ala | Ser | Leu | Pro | Leu | Phe | Pro | Gln | Arg | Ala | Ser |
| 1 | | | | 5 | | | | | 10 | | | | | 15 | |
| Arg | Leu | Arg | Pro | Ser | Leu | His | Pro | Asp | Ala | Arg | Val | Arg | Ala | Arg | Pro |
| | | | 20 | | | | | 25 | | | | | 30 | | |
| Pro | Ala | Arg | Pro | Pro | Val | Arg | Pro | Gln | Pro | Gly | Ala | Ser | Ala | Arg | Ser |
| | | | 35 | | | | | 40 | | | | | 45 | | |
| Ser | Ala | Phe | Ala | Ala | Ala | Pro | Leu | Ala | Ser | Thr | Leu | Pro | Pro | Gly | Pro |
| | 50 | | | | | 55 | | | | | 60 | | | | |
| Ala | Arg | Thr | Arg | Ala | Thr | Ala | Ala | Pro | Pro | Ala | Ala | Thr | Pro | Pro | Pro |
| 65 | | | | | 70 | | | | | 75 | | | | | 80 |
| Pro | Arg | Leu | Phe | Arg | Pro | Pro | Ala | Ala | Ala | Pro | Asp | Glu | Val | Met | Ala |
| | | | | 85 | | | | | 90 | | | | | 95 | |
| Thr | Ala | Asn | Phe | Gly | Lys | Ile | Gln | Ile | Gly | Ile | Tyr | Val | Glu | Ile | Lys |
| | | | 100 | | | | | 105 | | | | | 110 | | |
| Arg | Ser | Asp | Gly | Arg | Ile | His | Gln | Ala | Met | Val | Ala | Ser | Leu | Asn | Glu |
| | | 115 | | | | | 120 | | | | | 125 | | | |
| Asp | Asn | Glu | Ser | Val | Thr | Val | Glu | Trp | Ile | Glu | Asn | Gly | Asp | Thr | Lys |
| | | 130 | | | | | 135 | | | | | 140 | | | |
| Gly | Lys | Glu | Ile | Asp | Leu | Glu | Ser | Ile | Phe | Ser | Leu | Asn | Pro | Asp | Leu |
| 145 | | | | | 150 | | | | | 155 | | | | | 160 |
| Val | Pro | Asp | Glu | Asp | Ile | Glu | Pro | Ser | Pro | Glu | Leu | Pro | Pro | Pro | Ser |
| | | | | 165 | | | | | 170 | | | | | 175 | |
| Ser | Ser | Ser | Lys | Val | Asn | Lys | Ile | Val | Lys | Asn | Arg | Arg | Thr | Val | Ala |
| | | | 180 | | | | | 185 | | | | | 190 | | |
| Ala | Val | Lys | Asn | Asp | Pro | Pro | Arg | Asp | Asn | Arg | Val | Val | Gly | Ser | |
| | | 195 | | | | | 200 | | | | | 205 | | | |
| Ala | Arg | Ala | Arg | Pro | Ser | Gln | Leu | Pro | Glu | Gln | Ser | Ser | Ser | Ala | Gln |
| | 210 | | | | | 215 | | | | | 220 | | | | |
| Gln | Asn | Gly | Ser | Val | Ser | Asp | Ile | Ser | Pro | Val | Gln | Ala | Ala | Lys | Lys |
| 225 | | | | | 230 | | | | | 235 | | | | | 240 |
| Glu | Phe | Gly | Pro | Pro | Ser | Arg | Arg | Lys | Ser | Asn | Cys | Val | Lys | Glu | Val |
| | | | | 245 | | | | | 250 | | | | | 255 | |

```
Glu  Lys  Leu  Gln  Glu  Lys  Arg  Glu  Lys  Arg  Arg  Leu  Gln  Gln  Gln  Glu
               260                      265                      270

Leu  Arg  Glu  Lys  Arg  Ala  Gln  Asp  Val  Asp  Ala  Thr  Asn  Pro  Asn  Tyr
          275                      280                      285

Glu  Ile  Met  Cys  Met  Ile  Arg  Asp  Phe  Arg  Gly  Ser  Leu  Asp  Tyr  Arg
     290                      295                      300

Pro  Leu  Thr  Thr  Ala  Asp  Pro  Ile  Asp  Glu  His  Arg  Ile  Cys  Val  Cys
305                      310                      315                      320

Val  Arg  Lys  Arg  Pro  Leu  Asn  Lys  Lys
                    325
```

(2) INFORMATION FOR SEQ ID NO:8:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..90

(xi) SEQUENCE DESCRIPTION: SEQ ID NO:8:

```
AGC  GAA  AAA  AAA  AAA  CCA  AAA  GAA  CTA  AGA  CAT  GCC  ACC  CCC  GCC  CCG        48
Ser  Glu  Lys  Lys  Lys  Pro  Lys  Glu  Leu  Arg  His  Ala  Thr  Pro  Ala  Pro
  1                  5                         10                      15

CCC  CCA  CTT  CCA  CCC  CGC  AAT  GTT  GCT  TTT  CTT  GAT  GGT  TAATAATAAA          97
Pro  Pro  Leu  Pro  Pro  Arg  Asn  Val  Ala  Phe  Leu  Asp  Gly
               20                       25                  30

TACTGTCACG  TAGCTGTGTA  CAAAGAGATG  TGAAATACTT  TCAGGCAAAA  ATAAACTGTA              157

AGTGACTCAT  GAAAGTTGGC  CTTGCTGTGT  GGTTGTGGGG  GGTGGGGGGA  TGGACAGGGG              217

TGGGGGGGGG  GGATGTCTAT  GCAGGGAGGG  GGCAGGACAC  ACCT                                 261
```

(2) INFORMATION FOR SEQ ID NO:9:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:9:

```
Ser  Glu  Lys  Lys  Lys  Pro  Lys  Glu  Leu  Arg  His  Ala  Thr  Pro  Ala  Pro
  1                  5                         10                      15

Pro  Pro  Leu  Pro  Pro  Arg  Asn  Val  Ala  Phe  Leu  Asp  Gly
               20                       25
```

(2) INFORMATION FOR SEQ ID NO:10:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:10:

```
Ala  Pro  Thr  Met  Pro  Pro  Pro  Leu  Pro  Pro  Val  Pro  Pro  Gln  Pro  Ala
1              5                        10                       15

Arg
```

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:11:

```
Phe  Pro  Ala  Tyr  Pro  Pro  Pro  Pro  Val  Pro
1              5                        10
```

(2) INFORMATION FOR SEQ ID NO:12:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:12:

```
Ala  Pro  Pro  Thr  Pro  Pro  Pro  Leu  Pro  Pro
1              5                        10
```

(2) INFORMATION FOR SEQ ID NO:13:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:13:

```
Pro  Pro  Ala  Leu  Pro  Pro  Pro  Pro  Arg  Pro
1              5                        10
```

(2) INFORMATION FOR SEQ ID NO:14:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:14:

```
Pro  Pro  Asp  Asn  Gly  Pro  Pro  Pro  Leu  Pro
1              5                        10
```

(2) INFORMATION FOR SEQ ID NO:15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:15:

```
Pro  Pro  Gln  Met  Pro  Leu  Pro  Glu  Ile  Pro
1              5                        10
```

( 2 ) INFORMATION FOR SEQ ID NO:16:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Asp Glu Val Pro Val Pro Pro Pro Val Pro Pro Arg Arg
1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Thr Pro Ala Pro Pro Pro Leu Pro Pro Arg Asn Val
1               5                   10
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Gln Ser Arg Pro Leu Pro Ser Pro Pro Lys Phe Thr
1               5                   10
```

( 2 ) INFORMATION FOR SEQ ID NO:19:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Arg Arg Ala Pro Ala Val Pro Pro Ala Arg Pro Gly Ser
1               5                   10
```

( 2 ) INFORMATION FOR SEQ ID NO:20:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Ala His Pro Pro Ala Arg Pro Pro Val Arg Pro Gln Pro Gly
1               5                   10
```

( 2 ) INFORMATION FOR SEQ ID NO:21:

( i ) SEQUENCE CHARACTERISTICS:
        ( A ) LENGTH: 17 amino acids (B) TYPE: amino acid
(D) TOPOLOGY: linear (ii) MOLECULE TYPE: peptide (xi) SEQUENCE DESCRIPTION: SEQ ID NO:21:

Ala Pro Pro Ala Ala Thr Pro Pro Pro Pro Arg Leu Phe Arg Pro Pro
1               5                   10                  15
Ala (2) INFORMATION FOR SEQ ID NO:22:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:22:

Lys Pro Pro Thr Pro Pro Pro Glu Pro Glu Thr
1               5                   10

(2) INFORMATION FOR SEQ ID NO:23:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:23:

NNKNNKNNKN NKNNKNNKNN KNNKNNKNNK NNKNNKNNKN NKNNK                45

(2) INFORMATION FOR SEQ ID NO:24:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:24:

NNKNNKNNKN NKNNKNNK                                              18

(2) INFORMATION FOR SEQ ID NO:25:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:25:

GCCTGTAGCA TTCCACAGAC AA                                         22

(2) INFORMATION FOR SEQ ID NO:26:

(i) SEQUENCE CHARACTERISTICS:
    (A) LENGTH: 15 amino acids
    (B) TYPE: amino acid
    (D) TOPOLOGY: linear ( i i ) MOLECULE TYPE: peptide ( x i ) SEQUENCE DESCRIPTION: SEQ ID NO:26:

```
Trp Leu His Leu His Ser Arg Pro Leu Pro Ser Thr Pro His Asp
1               5                   10                  15
```

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Ala Gly Asp Arg Pro Leu Pro Pro Leu Pro Tyr Asn Pro Lys Ser
1               5                   10                  15
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
Leu Ala Leu Ala Arg Pro Leu Pro Val Pro Pro Trp Arg Gln Ile
1               5                   10                  15
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

```
Thr Gly Pro Arg Pro Leu Pro Leu Pro Pro Leu Arg Ser Met Ser
1               5                   10                  15
```

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

```
His Ser His Phe His Pro Arg Pro Leu Pro Pro Leu Pro Val Arg
1               5                   10                  15
```

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

```
   Ser  Phe  Arg  Pro  Leu  Pro  Pro  Leu  Pro  Gln  Phe  Leu  Pro  Met  Tyr
   1                  5                        10                       15
```

( 2 ) INFORMATION FOR SEQ ID NO:32:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:32:

```
   Ser  Thr  Leu  Met  Lys  Ile  Ser  Asn  Arg  Pro  Leu  Pro  Ala  Ala  Ser
   1                  5                        10                       15
```

( 2 ) INFORMATION FOR SEQ ID NO:33:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:33:

```
   Arg  Pro  Gly  Asp  Pro  Leu  Pro  Arg  Thr  Pro  Ile  Ala  Gly  Asp  Thr
   1                  5                        10                       15
```

( 2 ) INFORMATION FOR SEQ ID NO:34:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:34:

```
   Phe  Val  Gly  Asp  Pro  Leu  Pro  Tyr  Ile  Pro  His  Met  His  Trp  Phe
   1                  5                        10                       15
```

( 2 ) INFORMATION FOR SEQ ID NO:35:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:35:

```
   Arg  Pro  Leu  Pro  Ser  Pro  Pro
   1                  5
```

( 2 ) INFORMATION FOR SEQ ID NO:36:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:36:

```
   Leu  Ala  Arg  Pro  Leu  Pro  Val  Pro  Pro  Trp  Arg  Gln
   1                  5                        10
```

( 2 ) INFORMATION FOR SEQ ID NO:37:

```
        ( i ) SEQUENCE CHARACTERISTICS:
                ( A ) LENGTH: 7 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:37:

Arg  Pro  Leu  Pro  Val  Pro  Pro
      1                 5

( 2 ) INFORMATION FOR SEQ ID NO:38:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Region
                ( B ) LOCATION: 4
                ( D ) OTHER INFORMATION: /label=hydrophobic ( x i ) SEQUENCE DESCRIPTION: SEQ ID NO:38:

Pro  Pro  Pro  Xaa  Pro  Pro
      1                 5

( 2 ) INFORMATION FOR SEQ ID NO:39:

( i ) SEQUENCE CHARACTERISTICS:
                ( A ) LENGTH: 13 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:39:

Pro  Gln  His  Ser  Ala  Val  Pro  Pro  Arg  Pro  Gly  Pro  Ala
      1                 5                           10

( 2 ) INFORMATION FOR SEQ ID NO:40:

( i ) SEQUENCE CHARACTERISTICS:
                ( A ) LENGTH: 7 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:40:

Pro  Pro  Pro  Leu  Pro  Pro  Arg
      1                 5
```

EXPRESSION CLONING OF C-SRC SH3-DOMAIN BINDING PROTEINS

FIELD OF THE INVENTION

The present invention relates to the identification of 3 cDNAs based upon their ability to interact with the SH3 domain of c-src and which interact additionally with SH3 domains from other proteins. The present invention further relates to the identification of a novel heptamer amino acid motif identified by screening a phage random peptide library with the SH3 domain of c-src. The cDNAs, their SH3-binding motifs, or the novel heptamer amino acid motif identified by screening the phage random peptide library may be useful in inhibiting signal transduction, particularly in pathways involving c-src or src-like kinases, such as T-cell activation and bone resorption by osteoclasts. Additionally, various binding assays can be established using these components, and used to discover low molecular weight inhibitors of the signal transduction pathways in which they participate.

BACKGROUND OF THE INVENTION

Src-homology regions 2 and 3 (SH2 and SH3) are conserved sequence motifs consisting of approximately 100 and 60 amino acid residues, respectively, and found in many eukaryotic proteins with diverse functions (1–3). SH3 domains have been identified in several cytoskeleton-associated proteins such as p80/p85, myosin 1b, and spectrin, in the neutrophil NADPH oxidase-associated proteins p47 and p67, and in several yeast proteins important for morphogenesis (Bem1p and ABP-1), mating (FUS1) or for the regulation of ras activity (Cdc25 and Ste6; for review see Musacchio et al. (4)). The observation that many SH3-containing proteins are cytoskeleton-associated led to the suggestion that SH3 domains play a role in multimeric protein complex formation at or near cytoplasmic membranes. Some proteins which contain both SH2 and SH3 domains (e.g. Grb2—the mammalian homologue of Sem5 and drk-proteins from *C. elegans* and *drosophila*, respectively) perform the function of adaptor molecules by joining activated receptor tyrosine kinases with the p21 ras guanine nucleotide-releasing protein (GNRP) SOS. Grb2 and its homologues bind to phosphotyrosine on activated membrane-anchored receptor tyrosine kinases through their SH2 domain and to SOS through their amino- and carboxyterminal SH3 domains (5–9). These processes lead to translocation of SOS to the plasma membrane where ras proteins are located. Thus, SH3-containing and SH3-binding proteins are involved in a highly conserved signal transduction pathway from activated growth factor receptors to p21 ras.

The non receptor tyrosine kinase c-src consists of an SH3, SH2 and tyrosine kinase domain. c-src appears to be most important in the normal function of osteoclasts, as determined from studies of src-knock-out mice (10). The catalytic activity of c-src and other nonreceptor tyrosine kinases is inhibited by the intramolecular association of their intrinsic SH2 domain to a phosphorylated Tyr (position 527) in the carboxy-terminal tail. Recent data indicate that the intrinsic SH3 domain (in cooperation with the SH2 domain) may also participate in the regulation of the kinase activity of these enzymes. Deletion of the c-src SH3 domain reduces the phosphorylation of Tyr-527 by csk kinase, resulting in the upregulation of c-src kinase activity (11). In addition to the above, the c-src SH3 domain may contribute to the repression of src catalytic activity by stabilizing the conformation most favorable for the interaction between the src SH2 domain and the phosphorylated carboxy-terminal Tyr-527 residue (12). Several mutations in the src SH3 domain were reported to increase its catalytic activity and oncogenicity, and there are some indications that the N-terminal region of the src SH3 domain may be responsible for specific interactions with as yet unidentified negative regulators of src activity (13). Therefore, the SH3 domain in the src family kinases can also be considered as an internal, potential regulator of kinase activity functioning in cooperation with the SH2 domain.

Several src SH3 binding proteins were isolated by affinity purification from cytoskeleton-rich fractions of Balb/c 3T3 cells, and one of these proteins was identified as paxillin, a vinculin-binding cytoskeletal protein. Some other SH3 binding proteins identified by this method possessed kinase activity, and probably belong to the family of serine and/or threonine kinases (14).

Though the structural basis for the interaction of different SH2 domains with phosphotyrosine has been well studied (15–18), the interaction between SH3 domains and SH3 binding proteins is much less well characterized, partly because only a few SH3 binding proteins have been identified. The first reported SH3 binding protein (3BP-1) bound to the SH3 domain of the c-abl tyrosine kinase (and to the SH3 domain of c-src as well) through a proline-rich sequence (19). This protein was identified by using a glutathione S-transferase (GST) fusion protein, which included the SH3 region of the c-Abl proto oncogene, to probe a λgt11 cDNA expression library. The SH3 binding sequences in 3BP-1 and several other proteins identified in this work were localized to a nine or ten amino acid proline-rich motif, XPXXPPPΨXP (SEQ ID NO: 1, Ψ represents hydrophobic amino acid residues) (20). Similar motifs have since been recognized in several other proteins including the PI 3-kinase p85 subunit (21), dynamin (22), formin, and the acetylcholine muscarinic receptor (20). In several of these proteins the putative binding sites are multiple and overlapping (22).

The specificity of SH3 binding proteins toward different SH3 domains has been studied using the 3BP-1 protein (with Abl, Src, Neural Src, Crk-SH3 domains, (19)), dynamin (with 15 different SH3 domains, (22)), paxillin (with Src, neural Src, Lyn SH3-domains, (14)). These experiments demonstrate that most of the presently identified SH3 domain binding sequences have a broad spectrum of SH3 domains as possible binding partners (19, 22). On the other hand, no binding motifs have been identified for some SH3 domains which exhibit a low homology to the Src SH3 domain (e.g. the ras-GAP SH3 domain). Therefore, the identification of SH3 binding clones and identification of motifs recognized by SH3 domains represents an important step in understanding the determinants of specificity for this type of protein-protein interaction.

Random peptide libraries offer a unique, abundant and complex source of short peptides which can be used to identify specific binding sequences and core amino acid consensus sequences for virtually any screening agent. Successful screening of these libraries has been described not only for epitopes recognized by monoclonal antibodies (23–33), but also for the identification of peptide sequences interacting directly with other proteins such as the molecular chaperone BiP (34), calmodulin (35), $a_5b_1$ integrin (36), platelet glycoprotein IIb/IIIa (37), S-Protein (15, 38) streptavidin (39) and concanavalin A (40, 41).

Recently, Chen et al. (42) utilized the SH3 domain of PI3-kinase p85 to screen a biased combinatorial library of synthetic peptides in which prolines were fixed in three of nine positions with the six other positions being randomized. The bias for this library, represented by the formula XXX-PPXPXX (SEQ ID NO: 2), was derived from an alignment of the SH3-binding motifs in 3BP-1 and the guanine nucleotide exchange factor Sos1.

Various strategies have been employed to screen phage cDNA libraries for clones encoding proteins which interact with the screening agent. For example, phage cDNA libraries have been screened with antibodies, nucleic acids, and tyrosine-phosphorylated polypeptides. The identification of cDNA clones encoding proteins which interact with src SH3 domain, native (intact) c-src, or any segment of c-src has never previously been reported.

SUMMARY OF THE INVENTION

This invention provides a unique SH3 binding domain core motif of the sequence RPLPXXP (SEQ ID NO: 3) derived by screening a completely random bacteriophage peptide library with a Src SH3 containing protein.

Additionally, this invention provides 3 cDNA clones encoding proteins which interact with the SH3 domain of c-src, as well as the amino acid sequences which mediate this binding.

Another embodiment of this invention is a method of identifying SH3-binding proteins and elucidating the sequences which mediate binding. This method may be used as an assay to select compounds which bind to this site and which inhibit or enhance the binding of the SH3 domain.

Other and further objects, features and advantages will be apparent from the following description of the preferred embodiments of the invention given for the purpose of disclosure when taken in conjunction with the following drawings.

BRIEF DESCRIPTION OF THE FIGURES

FIG. 8 depicts a diagram and sequence of Src SH3 binding cDNA L35 (SEQ ID NOS: 8 and 9).

FIG. 9 demonstrates the reaction of electroblotted Src SH3 binding protein-gene 10 fusions with a panel of various SH3/GST fusion proteins.

FIG. 10 demonstrates the alignment of known SH3 binding motifs with homologous sequences from clones L14, L17 and L35 (SEQ ID NOS: 1 and 10–25).

Figure 1:
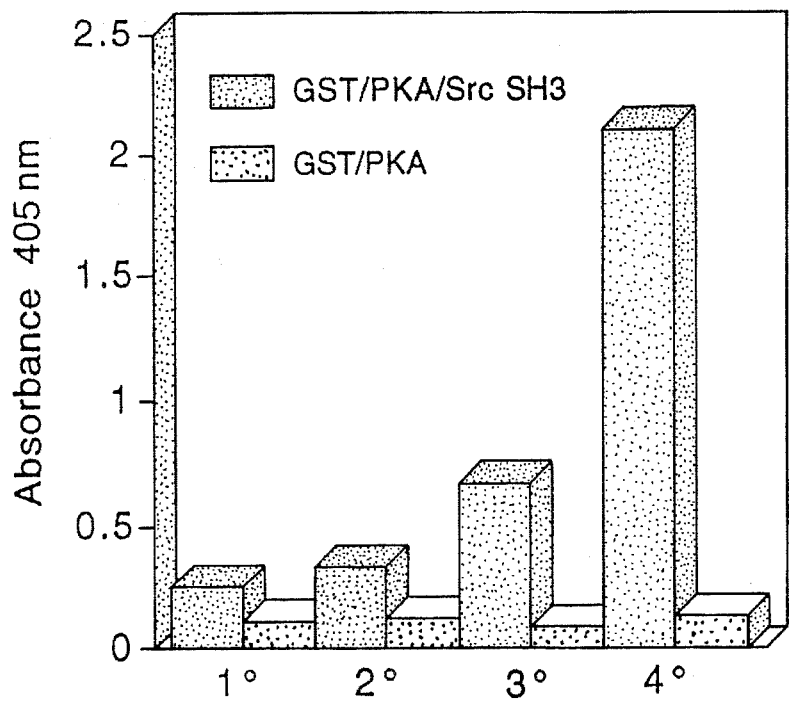
FIG. 1 shows a screen of the phage display library with GST/PKNSrc SH3. The phage display library was screened through 4 cycles of enrichment and amplification (1°–4°). At each cycle the phage were tested for their ability to bind to either immobilized GST/PKNSrc SH3 or GST/PKA only using an ELISA assay as described in Example 1.

The following examples describe the isolation, purification and measurement of biological activity of the proteinaceous factors and antibodies of the present invention and are not intended to be limiting unless so expressly stated.

EXAMPLE 1

Isolation of a Novel c-src SH3 Binding Motif by Screening a Phage Random Peptide Library A. Reagents, Peptides and Vectors Enzymes were purchased from New England Biolabs and Boehringer Mannheim. The site directed mutagenesis kit was purchased from Amersham. The fuse5 vector and bacterial strains were kindly provided by Dr. George Smith (University Of Missouri, Columbia). Glutathione Sepharose® was obtained from Pharmacia. AminoLink® coupling gel was obtained from Pierce. The coating, washing, and blocking/dilution buffers used in the library screen and in ELISA assays were obtained from 5 Prime→3 Prime, Inc. Immulon microtiter trays were purchased from Dynatech Laboratories Inc.

A GST vector (GST/Src SH3) encoding the Src SH3 domain (amino acids 84–148) was kindly provided by Dr. I. Gout (Ludwig Institute for Cancer Research, London). A cDNA containing the SH3 domain of chicken c-Fyn was amplified by the polymerase chain reaction and cloned into the pGEX-2T vector at the BamHI-EcoRI sites. A GST vector containing the Ras-GAP SH3 was kindly provided by Dr. Bruno Tocqué (Rhône-Poulenc Rorer, Vitry). Radiolabeled GST/Src SH3 and control GST protein were prepared as described by Ron and Dressler (43). Briefly, oligonucleotides encoding a specific site for phosphorylation by protein kinase A (PKA) were annealed and ligated into the BamHI site of the GST/Src SH3 vector and the GST vector. The purified GST/PKA/Src SH3 and GST/PKA fusion proteins were phosphorylated in vitro using the catalytic subunit of protein kinase A and [g-$^{32}$P-ATP]. Three μg of fusion protein was reacted for 1 hour at 30° C. in 50 mM phosphate buffer pH 8.0, 10 mM MgCl$_2$, 4 mM DTT, 5 mM NaF, 75 u/ml of protein kinase A catalytic subunit (Sigma) and 100 μCi of [γ-$^{32}$P]-ATP (NEN) in a total volume of 100 μl. The labeled protein was purified by chromatography on glutathione-Sepharose® and had a specific activity of approximately 1–2×10$^5$ dpm/ng.

B. Expression and Purification of GST and GST/SrcSH3 protein

*Escherichia coli* XL1-Blue cells containing GST, GST/SrcSH3 or GST/PKNSrcSH3 fusion constructs were grown overnight in LB containing 100 μg/ml ampicillin (LB/amp). Overnight cultures were diluted 1:50 in fresh LB/amp (1 liter) and cells were grown to an O.D.$_{550}$ of 0.3 at 37° C., induced with 1 mM isopropyl-β-D-thiogalactopyranoside (IPTG), and grown for an additional three hours. Cells were harvested by centrifugation, washed once with phosphate buffered saline (PBS), resuspended in a small volume of PBS (10–20 ml) containing a mixture of proteinase inhibitors including pepstatin A (0.25 μg/ml), aprotinin (0.5 μg/ml), leupeptin (0.25 μg/ml), and PMSF (1 mM). Cells were sonicated on ice and the cell lysates were centrifuged at 12,000×g for 30 min. Supernatant fractions were reacted for 30 min at 4° C. with 1 ml of a 50% slurry of glutathione Sepharose, washed twice with 50 ml of PBS (at 4° C.) and the bound GST fusion proteins were eluted by reaction for 15 min at 4° C. with 1.5 ml freshly prepared reduced glutathione. Protein was quantified by measuring the absorbance at 280 nm followed by characterization by SDS polyacrylamide gel electrophoresis.

C. Library Construction

A fusion phage library was constructed in the filamentous bacteriophage fuse 5B, a vector derived from fd filamentous phage (44). The fuse5B vector was constructed from the vector fuse5 (27) by removal of a downstream BstXI site in fuse5 followed by replacement of the SfiI cloning site in gene III with a BstXI cloning site. Site directed mutagenesis was carried out using the oligonucleotide described by Cwirla et al.(29). For construction of the library a collection of oligonucleotides encoding all possible 15-mer peptides was synthesized on an Applied Biosystems Model 394 DNA synthesizer. The sequence of the degenerate oligonucleotide as well as the two half-site oligonucleotides was as described by Cwirla et al. (29) with the exception that $(NNK)_{15}$ (SEQ ID NO: 23) was used instead of $(NNK)_6$ (SEQ ID NO: 24) in the degenerate oligonucleotide sequence. The three oligonucleotides were phosphorylated with T4 polynucleotide kinase and then annealed with BstXI digested fuse5B DNA followed by overnight ligation at 15° C. The ligation products were precipitated with ethanol, redissolved in water and then electroporated into electrocompetent *E. coli* MC1061 cells using a BTX model 600 electroporation apparatus, yielding $5 \times 10^7$ independent transformants. This level of complexity should allow for the presence of virtually all possible hexamer sequences ($20^6 = 6.4 \times 10^7$ sequences) especially when one considers that each 15-mer contains 10 nested hexamer sequences. Nucleotide sequence analysis of random clones from this library indicated that greater than 50% of the clones contained an inserted sequence with an open reading frame (data not shown).

D. Library Screening

The GST/PKA/SrcSH3 fusion protein was immobilized at a concentration of 20 μg/ml in coating buffer in individual microtiter wells and incubated overnight at 4° C. The wells were blocked for one hour with 1X blocking/dilution buffer and rinsed 5 times with washing buffer. Approximately $1 \times 10^{11}$ tetracycline transducing units (TTU) of fusion phage in 1X blocking/dilution buffer was allowed to bind overnight at 4° C. The microtiter wells were then rinsed 5 times with washing buffer followed by the two elutions of bound phage with 0.2 ml of 50 mM sodium citrate, pH 2, 150 mM NaCl, for 5 min at room temperature. Phage elutions were pooled, neutralized and then amplified by reinfection into *E. coli* K 91-Kan cells (44). This process was repeated three times prior to analysis of the clones by DNA sequencing. Phage collected from the amplifications corresponding to each of four cycles of enrichment were tested for specific binding to GST/PKNSrc SH3 protein using a microtiter plate assay. Phage bound to the immobilized GST/PKA/Src SH3 were detected in this assay using a biotinylated polyclonal anti-M13 antibody and phage detection ELISA system (5 Prime→3 Prime) according to the manufacturer's recommended conditions. In brief, individual microtiter wells were coated overnight at 4° C. with a 2 μg/ml solution of Src SH3/PKNGST or GST/PKA in coating buffer. Several concentrations of phage were initially tested for obtaining an optimal signal to background ratio. Phage (0.2 ml) from pools of all four amplifications of the GST/PKNSrcSH3 fuse5B library screen were allowed to react with the immobilized GST proteins for two hours at room temperature. The microtiter wells were then washed, reacted for one hour with biotinylated anti-M13 polyclonal antibodies, washed again and then reacted with streptavidin conjugated alkaline phosphatase for 30 min. Following further washes, the reaction was developed with p-nitrophenyl phosphate in diethanolamine buffer and the absorbance at 405 nm measured. In order to confirm the titer of each phage sample reacted in this experiment, aliquots of each sample were tested simultaneously by reaction with immobilized nonbiotinylated anti-M13 antibodies supplied by the manufacturer. Detection of bound phage was then performed with the biotinylated anti-M13 antibody as described above. The results of this experiment (FIG. 1) demonstrated a pattern of specific binding to GST/PKA/Src SH3 with an increase in enrichment after each round of selection. Binding to the control GST/PKA protein was minimal throughout the experiment.

At the end of 4 rounds of screening, phage single stranded DNA was isolated from 45 clones by polyethylene glycol precipitation, phenol-chloroform extraction, and ethanol precipitation and used for dideoxynucleotide sequencing using [α-$^{35}$S]dATP and Sequenase T7 DNA Polymerase, essentially as per the manufacturer's instructions (United States Biochemical). An antisense oligonucleotide, 5'GCCTGTAGCATTCCACAGACAA3'(SEQ ID NO: 25), specific for the fuse5B vector downstream of the cloning site, was used as the sequencing primer. The DNA sequence from eight isolates could not be clearly established and these clones were not pursued further. The deduced amino acid sequence of the remaining clones is shown in Table 1.

TABLE 1

| Sequence Name | Peptide Sequence | Number of Isolates | Relative Binding (%) |
|---|---|---|---|
| Lambda 14 | Q S R P L P S P P K F T | | 75 |
| fuse5B-4.2 | W L H L H S R P L P S T P H D | 17 | 85 |
| fuse5B-4.25 | A G D R P L P P L P Y N P K S | 8 | 80 |
| fuse5B-4.3 | L A L A R P L P V P P W R Q I | 2 | 80 |
| fuse5B-4.27 | T G P R P L P L P P L P S M S | 2 | 76 |
| fuse5B-4.51 | H S H F H P R P L P P L P V R | 1 | 75 |
| fuse5B-4.16 | S F R P L P P L P Q F L P M Y | 2 | 72 |
| fuse5B-4.53 | S T L M K I S N R P L P A A S | 2 | 22 |
| fuse5B-4.46 | R P G D P L P R T P I A G D T | 2 | 9 |
| fuse5B-4.24 | F V G D P L P Y I P H M H W F | 1 | 4 |

Table 1 shows the Src SH3 binding sequences (SEQ ID NOS: 26–34) derived from screening the fuse 5B phage display library. Phage derived sequences are arranged according to a common consensus SH3 binding domain motif. This consensus sequence is also displayed in a SH3 binding domain motif (SEQ ID NO: 18) identified in a protein (Lambda 14) which was isolated during a screen of a mouse embryo cDNA library with Src SH3 (see Example 2). The frequency of appearance of each isolate is indicated. The relative binding strength of peptides corresponding to each sequence was determined, as in FIG. 2, by calculating the % of $^{32}$P-labeled GST/PKNSrc SH3 or control $^{32}$P-labeled GST/PKA proteins precipitated with peptides covalently attached to AminoLink® resin. The % of bound ligand was calculated as bound (cpm)/total (cpm)×100%. The peptides correspond to a negative control (SV40 peptide) or the sequences derived from either the cDNA (lambda 14) or the phage library (fuse 5B 4.3) screens. The peptides tested were as follows:

| | |
|---|---|
| KPPTPPPEPET | SV40-peptide (11 mer) (SEQ ID NO: 22) |
| QSRPLPSPPKFT | Lambda 14 (12 mer) (SEQ ID NO: 18) |
| RPLPSPP | Lambda 14 (7 mer) (SEQ ID NO: 35) |
| LALARPLPVPPWRQI | fuse5B 4.3–15 (15 mer) (SEQ ID NO: 28) |
| LARPLPVPPWRQ | fuse5B 4.3–12 (12 mer) (SEQ ID NO: 36) |
| RPLPVPP | fuse5B 4.3–7 (7 mer) (SEQ ID NO: 37) |

These 37 clones comprised only 9 different sequences, many of which were repeated several or more times as indicated. Further examination of these sequences revealed a highly reiterated, proline-rich, 7 amino acid consensus sequence, RPLPXXP (SEQ ID NO: 3), contained within the sequence of the clones examined. This motif demonstrated a strong similarity to a Src SH3 binding sequence identified within a protein (lambda 14) isolated by screening of a lambda-lox mouse embryo cDNA library with a $^{32}$P-labeled Src SH3 domain probe. This work is described in Example 2.

At least three of the phage derived sequences (fuse5B 4.2, fuse5B 4.3 and fuse5B 4.27) exhibited identity in six out of seven amino acids when compared with the lambda 14 sequence. Six out of nine phage derived sequences were identical with the lambda 14 clone in five out of seven amino acid residues. The phage clone (fuse5B 4.2) isolated with the highest frequency (17/37), exhibited identity in seven out of eight amino acids when compared with the lambda 14 sequence.

E. Analysis of srcSH3 binding motif using synthetic peptides

Based on these data, peptides representing the lambda 14 sequence and the sequences isolated from the phage library were synthesized, coupled to a resin, and then tested for the ability to specifically and quantitatively precipitate $^{32}$P-labeled GST/PKA/Src SH3 protein. Peptides were constructed manually using a custom built apparatus designed for the rapid simultaneous synthesis of 0.01–0.02 mmoles of peptide. Solid phase methodology using a 9-fluorenylmethyloxy carbonyl (FMOC) protection scheme in conjunction with the HOBT/Hbtu activation chemistry (45) was used. Peptides of interest were subsequently constructed in larger quantities (0.1–0.25 mmoles) using an Applied Biosystems Model 430 Peptide Synthesizer running Applied Biosystems Fast-moc® coupling cycle. All peptides were cleaved for 1.5 hours at room temperature using a cleavage reagent of 82.5% trifluoroacetic acid, 5% phenol, 5% H$_2$O, 5% thioanisole, and 2.5% ethanedithiol (46). Following cleavage, the peptides were precipitated with ether, washed, then dried for 1 hour under vacuum. The peptides were then solubilized in either water, 10% acetic acid, or 10 mM ammonium bicarbonate depending upon the peptides net charge or solubility. Peptides were analyzed by reverse phase HPLC for purity and by ion spray mass spectrometry for molecular weight integrity. A purity level of 95% was achieved for all peptides along with correct mass spectrometry data. Lyophilized peptides were dissolved in H$_2$O and coupled to AminoLink® coupling gel. The efficiency of coupling was measured by analyzing the peptide solution, before and after coupling, by reverse phase HPLC and by reading the absorbance at 220 nm. Both methods demonstrated greater than 70% coupling efficiency for all peptides.

An aliquot of the resin with covalently bound peptide (20 ml of wet beads, containing ~150 ng of peptide) was incubated with ~5 ng of either $^{32}$P-labeled GST/PKA/SrcSH3 fusion protein or $^{32}$P-labeled GST/PKA fusion protein, lacking the SH3 domain, as control. Incubations were carried out with approximately 5×10$^5$ cpm of protein (5 ng) in PBS buffer, pH 7.0, containing 5% BSA and 0.1% Tween 20. After a 30 min incubation at room temperature, the beads were extensively washed by centrifugation with PBS containing Triton X-100 until no radioactivity was detected in the wash buffer. The amount of bound GST/PKA/SrcSH3 and GST/PKA proteins was detected by Cherenkov counting and expressed as the percent of the bound versus the total added cpm. Results of this experiment are presented in Table 1 and demonstrate that the phage sequence fuse5B 4.2, isolated in highest abundance in the phage library screen, has a very strong binding capacity toward the Src SH3 domain. All but three of the sequences obtained in the screen exhibited this strong binding capacity. Clones that showed weaker binding contained substitutions for either the $NH_2$-terminal arginine residue or the COOH-terminal proline residue.

Figure 2A:
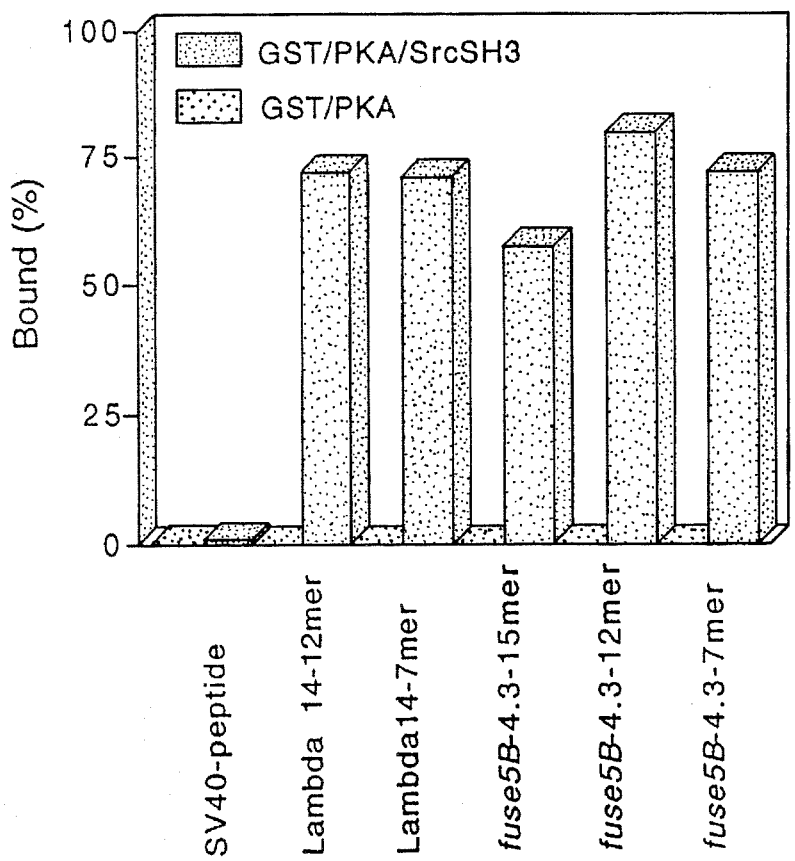
FIG. 2 demonstrates the analysis of Src SH3 domain binding to synthetic peptides. Panel A represents a bar chart depicting the % of $^{32}$P-labeled GST/PKNSrc SH3 or control $^{32}$P-labeled GST/PKA proteins precipitated with peptides covalently attached to AminoLink® resin. Panel B demonstrates an autoradiograph of a polyacrylamide gel containing radiolabelled Src SH3 protein precipitated with SH3 binding peptides covalently attached to the resin.
Figure 2B:
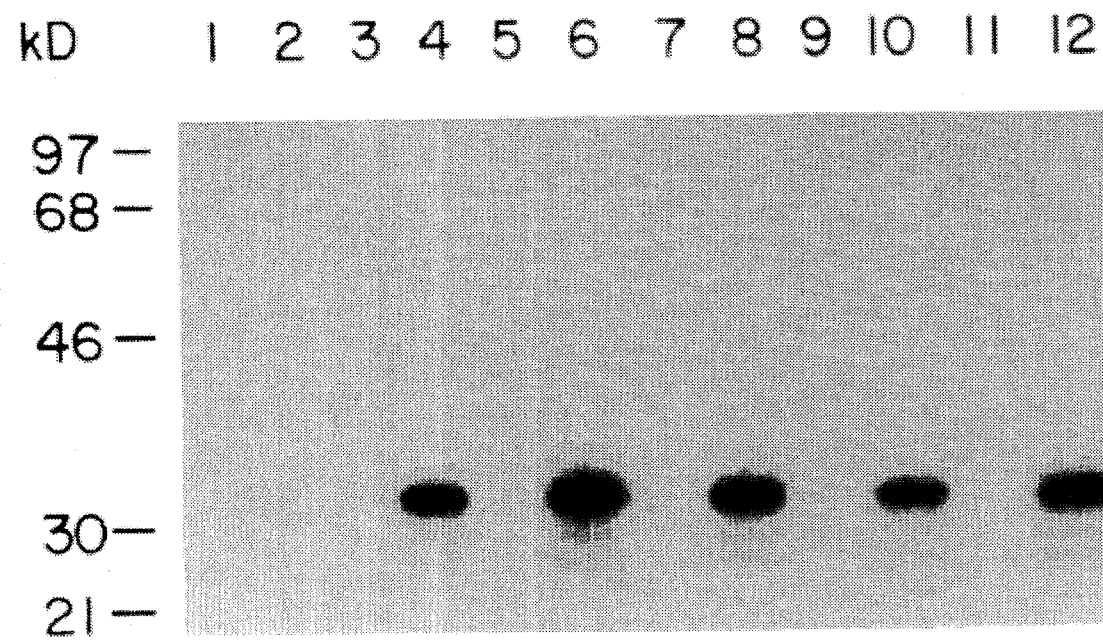

In order to define the core sequence responsible for binding in a more precise manner, a series of truncated peptides, based upon the lambda 14 sequence and the 4.3 clone isolated from the phage library, were also tested for the ability to specifically and quantitatively precipitate $^{32}$P-labeled GST/PKA/Src SH3 protein (FIG. 2A). Additionally, an aliquot of the radiolabeled Src SH3 domain bound to the immobilized peptide was also analyzed on SDS polyacrylamide gels (FIG. 2B). FIG. 2, panel B demonstrates an autoradiograph of a polyacrylamide gel containing radiolabelled Src SH3 protein precipitated with SH3 binding peptides covalently attached to the resin. The gel lanes correspond with samples as shown in the bar graph on FIG. 2, panel A. Samples of $^{32}$P-labeled GST/PKNSrc SH3 protein precipitated by the various SH3 binding peptides are shown in the even-numbered lanes while samples of the precipitated control $^{32}$P-labeled GST/PKA protein are shown in the odd-numbered lanes. The 7-mer sequence from both the phage derived and the cDNA derived SH3 binding domain sequences, appears to retain virtually all of the SH3 binding activity of the parental 15mer sequences. The fact that the 7-mer fuse5B 4.3 sequence has strong homology with the lambda-14 Src SH3-binding motif probably explains their indistinguishable activity in this assay. The specificity of the Src SH3-binding sequences for the Src SH3 domain is most clearly illustrated by the low binding of these sequences to $^{32}$P-labeled GST/PKA, which exhibits approximately a 100 fold lower binding to all peptides than does GST/PKNSrc SH3. In addition, a non-specific but otherwise proline-rich peptide (FIG. 2, SV40 peptide) also failed to display any significant binding.

We next demonstrated that the fuse5B 4.3 peptide retained its ability to bind Src SH3 even when the peptide was placed within the context of a larger protein sequence. For this experiment, oligonucleotides that encoded this 7 amino acid region of the 4.3 sequence were cloned into the GST vector in such a way that the seven amino acid peptide was expressed as a fusion protein with the GST sequence. *E. coil* lysates containing either the GST fusion protein or the GST protein only were subjected to SDS polyacrylamide gel electrophoresis, transferred to nitrocellulose and then probed with a $^{32}$P-labeled Src SH3 probe.

Figure 3:
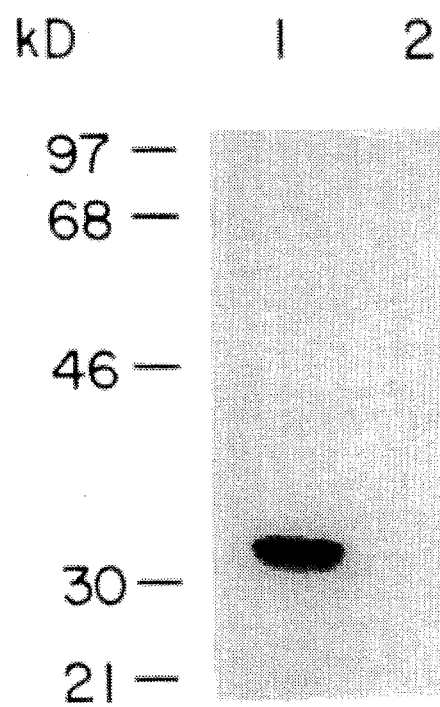
FIG. 3 depicts the binding of radiolabeled GST/PKNSrc SH3 protein to the fuse 5B 4.3 phage sequence expressed as a GST fusion protein in *E. coli.*

FIG. 3 depicts the binding of radiolabeled GST/PKNSrc SH3 protein to the fuse 5B 4.3 phage sequence expressed as a GST fusion protein in *E. coli*. Oligonucleotides encoding the sequence RPLPVPP from the fuse 5B 4.3 phage sequence were synthesized, annealed, ligated into the pGEX-2T GST expression vector, and transformed into *E. coli*. Cell cultures containing either GST fuse 5B 4.3 or GST only were grown to mid-log phase and induced with IPTG. Cells from the induced cultures were harvested, lysed in SDS-loading buffer, electrophoresed on an SDS polyacrylamide gel, and transferred to a nitrocellulose membrane. The membrane was then reacted with radiolabeled GST/PKNSrc SH3 protein. Lane 1. Lysate from GST fuse 5B 4.3, Lane 2. Lysate from GST only. The Src SH3 probe reacted with the GST fusion protein containing the fuse5B 4.3 7-mer, while no reaction was obtained with GST only.

Figure 4:
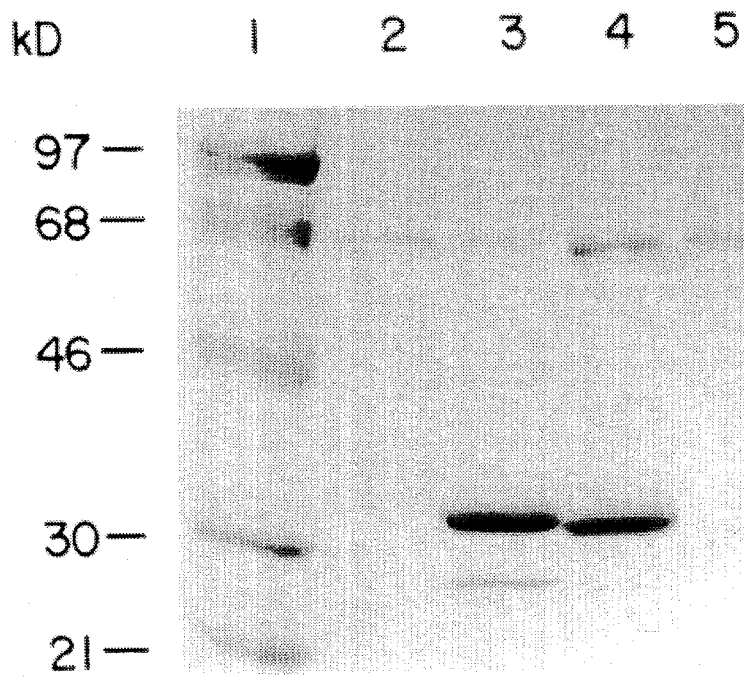
FIG. 4 shows an SDS polyacrylamide gel demonstrating the specificity of SH3 domain binding by a phage identified peptide.

Finally, in order to demonstrate specificity of the interaction of the Src SH3 domain with the sequences identified here, the fuse5B 4.3 sequence immobilized to resin, was reacted with different SH3 containing GST fusion proteins including the Fyn SH3 and Ras-GAP SH3. FIG. 4 shows an SDS polyacrylamide gel demonstrating the specificity of SH3 domain binding by a phage identified peptide. Various GST/SH3 fusion proteins as well as GST only were reacted with the Src SH3 binding peptide, fuse 5B 4.3–12 (as described for FIG. 2), covalently attached to AminoLink® resin. Precipitated proteins remaining after washing were electrophoresed on an and the gel was then stained with Coomassie Blue. Lane 1. Molecular weight markers, Lane 2. GST only, Lane 3. GST/Src SH3, Lane 4.—GST/Fyn SH3, Lane 5. GST/Ras-GAP SH3. The fuse5B 4.3 sequence was able to precipitate the Src SH3 and the closely related (8) Fyn SH3, but failed to react with the Ras-GAP SH3.

Recently, Chen et al. (42) utilized the SH3 domain of PI3-kinase p85 to screen a biased combinatorial library of synthetic peptides in which prolines were fixed in three of nine positions with the six other positions being randomized. The bias for this library, represented by the formula XXX-PPXPXX (SEQ ID NO: 3), was derived from an alignment of the SH3-binding motifs in 3BP-1 and the guanine nucleotide exchange factor Sos1. Although the biased combinatorial approach (42) can be successfully employed, the sequences which are identified by this technique are obviously influenced by the underlying assumptions (biases). This is avoided by the use of a completely random phage library. Additional advantages of the phage display library for the identification of SH3 binding motifs is that it is a rapid and convenient method, requiring approximately one week to perform three rounds of phage selection and amplification. The data presented herein, and that of Chen et al.(42) illustrate that at least some SH3 binding motifs consist of as little as 6–7 amino acids. Thus, the identification of additional binding motifs for specific SH3 domains should be possible by further application of the phage peptide library approach. This approach should facilitate the rapid identification of binding motifs for specific SH3 domains and should also provide a groundwork for a more detailed analysis of structure/function relationships.

EXAMPLE 2

Expression Cloning of Novel c-src Binding Proteins

Figures 5A, 5B:
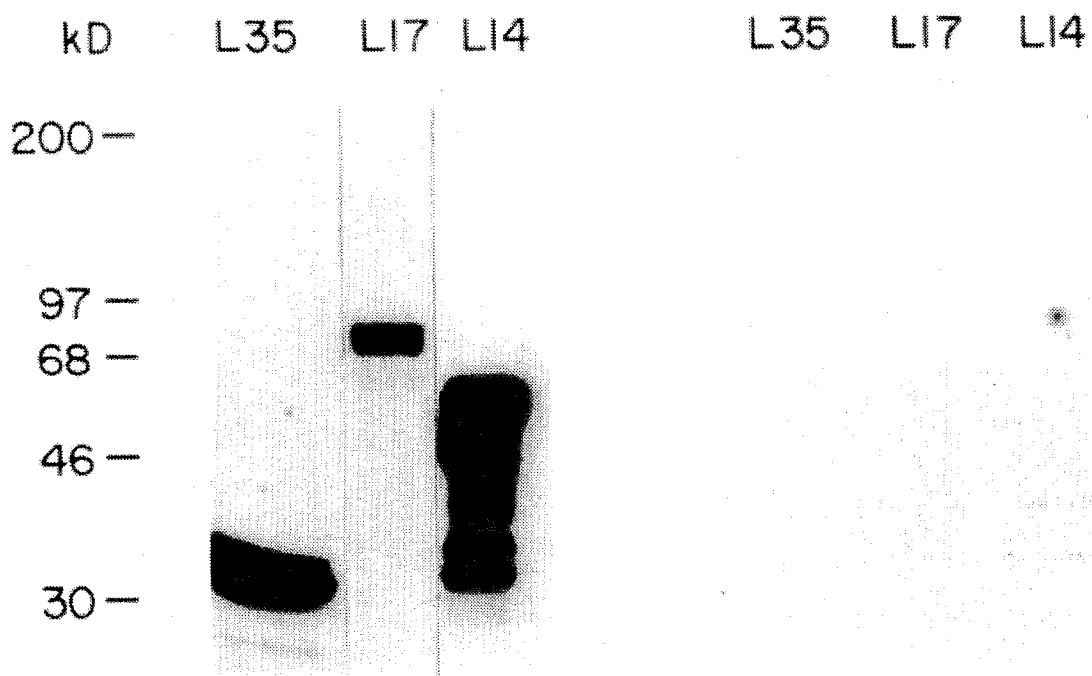
FIG. 5 shows autoradiographs demonstrating the reaction of src SH3 binding protein fusions with radiolabelled src SH3. Duplicate blots were reacted with either $^{32}$P labeled GST/PKNsrc SH3 (panel A) or with $^{32}$P labeled GST/PKA (panel B). After washing, blots were exposed to X-ray film.

A. Identification of cDNA clones encoding proteins which interact with src SH3 domain A mouse 12 day embryo cDNA library constructed in λEXlox (Novagen) was screened as follows: 1.4×10⁶ library phage were used to infect logarithmically growing *E. coli* BL21 (DE3)pLysE on forty 150 mm plates. Plates were incubated for 8 hrs at 37° C. and then overlayed with nitrocellulose (NC) circles presoaked and dried in 10 mM IPTG. The IPTG induces expression of the T7 RNA polymerase present on the host chromosome within a lamba lysogen. Plates were incubated an additional 12–16 hrs at 37° C., the NC circles were removed and washed thoroughly in TTBS (0.1% Triton X-100 in Tris buffered saline) to remove bacterial debris. The filters were blocked in 5% non fat dry milk in TTBS (blotto) for 2–16 hr at RT with gentle mixing. Filters were then reacted with 10–50 ng/ml labeled Src SH3 probe ($^{32}$P-GST/PKNSrc SH3) in fresh blotto (2 ml/filter) with gentle agitation overnight at room temperature. Filters were washed with large volumes of TTBS several times and then dried and exposed to X-ray film overnight. Three reacting plaques were recovered and subjected to several rounds of plaque purification using this proceedure. Primary lysates were prepared of pure clones, and phage from these were used to infect E. coli BM25.8 for automatic subcloning of the pEXlox cDNAs. To verify the interaction of the c-src SH3 domain with the cDNA-encoded proteins, the three positive λEXlox clones were converted to plasmids and introduced into E. coli pLysE. After addition of IPTG, cells were incubated 2 hours at 37° C. for expression of the recombinant fusion proteins. Cells were lysed in SDS loading buffer, proteins were resolved by SDS-PAGE, transferred to nitrocellulose, probed with either $^{32}$P-GST/PKN-Src SH3 or $^{32}$P-GST/PKA as control, and detected by autoradiography. FIG. 5 depicts the autoradiographs demonstrating the reaction of src SH3 binding protein fusions with radiolabelled src SH3. Inductions of the Src SH3 binding protein-gene 10 fusions from pEXlox clones (L35, L17, and L14) were run on SDS-PAGE gels and transfered to nitrocellulose. Duplicate blots were reacted with either $^{32}$P labeled GST/PKNsrc SH3 (panel A) or with $^{32}$P labeled GST/PKA (panel B). After washing, blots were exposed to X-ray film. The mobility of MW markers is indicated, and the loading order of inductions are shown on top of each panel. Clones L14, L17, and L35, respectively, produced fusion proteins of 66, 72, and 35 kDa, which bound only to the $^{32}$P-GST/PKNSrc SH3 probe (FIG. 5a) but not to the control $^{32}$P-GST/PKA probe (FIG. 5b). No binding to either probe was observed with lysates from non IPTG-induced cultures (data not shown). Taking into account the molecular weight of the T7 gene 10 protein (27.4 kDa) in each of these fusions, the apparent molecular weights of the cDNA-encoded polypeptides are 38–40, about 48, and 3–5 kDa for clones L14, L17, and L35, respectively.

B. Analysis of pEXlox cDNAs

The nucleotide sequences of the cDNA inserts of clones L14 (SEQ ID NO: 4), L17 (SEQ ID NO: 6), and L35 (SEQ ID NO: 8), were determined using Sequenase T7 DNA Polymerase, essentially as described in Example 1. Nucleotide sequence analysis of clone L14 (1168 bp) and comparison to DNA and protein databases revealed a 221 bp region with approximately 90% identity to an anonymous cDNA (EST06380) directionally cloned from a human infant brain cDNA library (47). FIG. 6 depicts a diagram and sequence of the Src SH3 binding cDNA L14. Also shown is a diagram of the human infant brain cDNA EST06380 (47) aligned to show the regions of homology between the two sequences, with the boundary positions marked. Position 1 is the first base of the L14 sequence after the EcoRI site of the vector, position 1168 is the last base of the insert before the HindIII site of the vector. The EST06380 homologous sequence is boxed. Putative SH3 binding domains (L14-1 and L14-2) and the putative polyA addition signal site are underlined. The internal HindIII site at position 532 used to generate the truncated version of L14 is shown and possible sites for tyrosine phosphorylation are indicated by a bold Y.

Figure 6A:
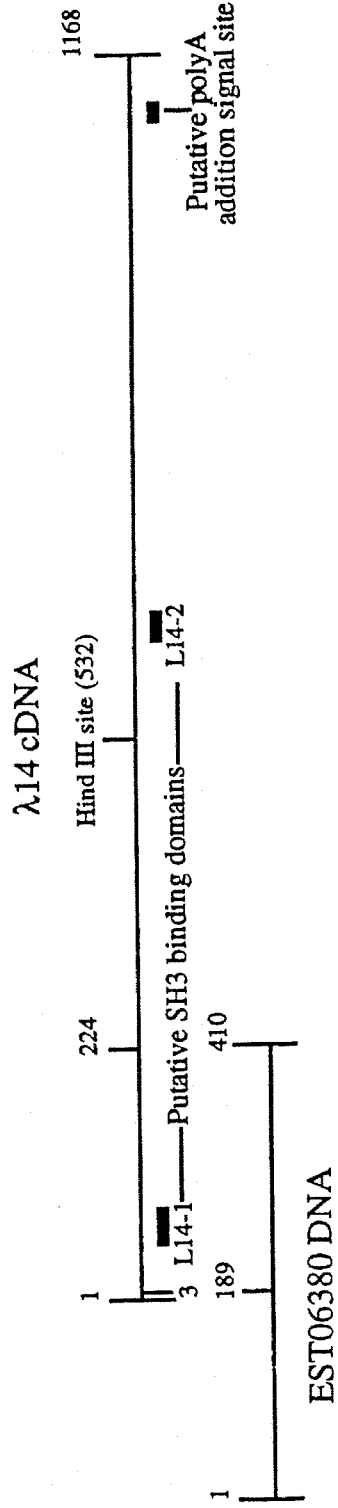
FIG. 6 depicts a diagram and sequence of the Src SH3 binding cDNA L14 (SEQ ID NOS: 4 and 5) and a diagram of the human infant brain cDNA EST06380 aligned to show the regions of homology between the two sequences.

Two proline-rich putative SH3-binding sequences were identifiable within the deduced amino acid sequence of L14 (FIGS. 6a, b). Experiments to determine which of these sequences were responsible for binding of the L14 fusion protein to the c-src SH3 domain are described below. The longest deduced open reading frame within clone L14 encodes a 370-residue protein with a predicted molecular weight of about 40 kDa, in close agreement with that deduced from the electrophoretic mobility of the L14 fusion protein (FIG. 5).

Figure 7A:
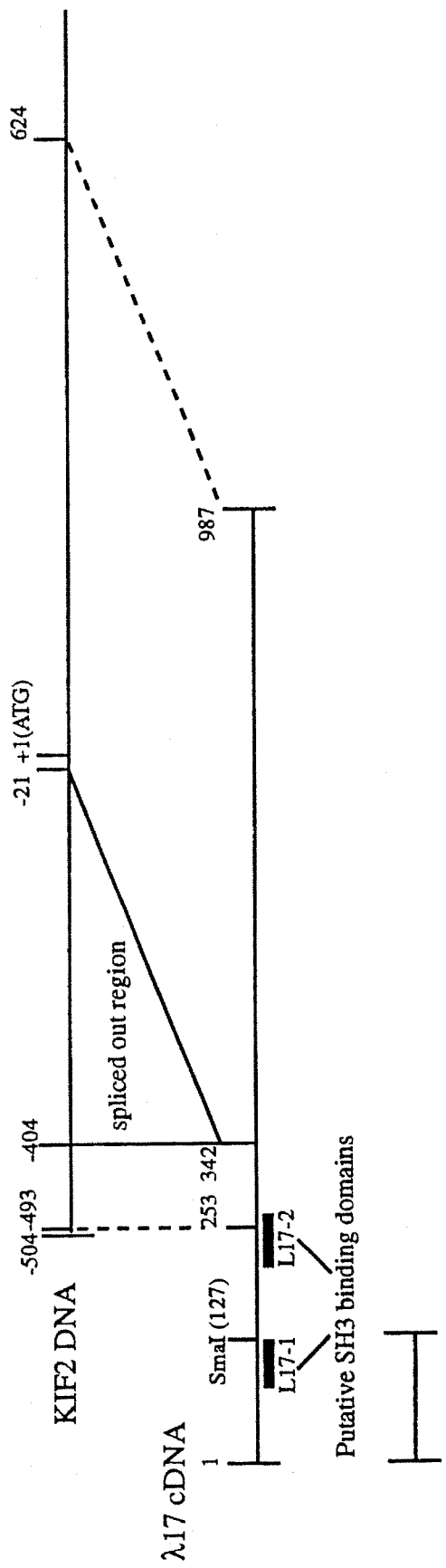
FIG. 7 depicts a diagram and sequence of the Src SH3 binding cDNA L17 (SEQ ID NOS: 6 and 7).

Nucleotide sequence analysis of clone L17 (987 bp) and comparison to DNA and protein databases revealed 99.9% identity of L17 with two segments of sequence of mouse kinesin-like-protein (KIF-2) (48). L17 consists of a 253 bp sequence, not reported in the KIF-2 sequence, followed by 89 bp of KIF-2 5' untranslated sequence, followed by a second region of 645 bp of KIF-2 sequence which contains the KIF-2 translation initiation codon (FIGS. 7a,b). Although these two KIF-2 sequences are contiguous within the sequence of L17, they are separated by 383 bp in the KIF-2 sequence (48). Thus, it appears that L17 is the product of alternative splicing of the KIF-2 gene, in which initiation of translation occurs upstream of the start codon normally utilized by KIF-2, resulting in the translation of sequences previously ascribed to the 5' untranslated region of KIF-2. Importantly, two proline-rich putative SH3-binding sequences are found within this region of L17. Experiments to determine which of these sequences were responsible for binding of the L17 fusion protein to the c-src SH3 domain (FIG. 5) are described below. Finally, the longest deduced open reading frame within clone L17 encodes a 329-residue protein with a calculated molecular weight of about 40 kDa. The reason why the L17 fusion protein has an abnormally slow mobility on SDS-PAGE (migrating with an apparent molecular weight of 48 kDa after subtraction of the mass of the T7 gene 10 protein sequences) is unclear. This may be due to the high content of prolines within the amino-terminal third of the L17 protein.

FIG. 7 depicts a diagram and sequence of the Src SH3 binding cDNA L17. The diagram represents the full length of the L17 cDNA isolate and shows the alignment to the homologous sequence of the mouse kinesin like gene KIF-2 (48). Position 1 is the first base of the insert sequence after the EcoRI site of the vector, and position 987 is the last base of the insert before the HindIII site of the vector. Nucleotides 1–252 of L17 are unique, while sequence 253–987 (boxed) is homologous to KIF-2 sequence. The region 253–342 of L17 corresponds to the sequence −493 to −404 of the KIF-2 5' untranslated and nucleotides 343 to 987 of L17 corespond to −21 to 624 of the KIF-2 sequence. In L17, nucleotides −404 and −21 of KIF-2 are adjacent. Thus, L17 appears to be an alternatively spliced form of KIF-2 in which a portion (nucleotides −403 to −22) of the untranslated region of KIF-2 is deleted and another (nucleotides −493 to −404) forms part of the open reading frame in L17. Nucleotides 1–252 of L17 which form part of the open reading frame in this clone may represent part of an upstream exon of the KIF-2 gene. The SmaI site at position 127 of L17 which was used to create a truncated version of L17 which contained only the L17-1 putative SH3 binding site is indicated. The region 1–127 was used to generate a non KIF-2 probe for northern hybridizations, and is indicated below the L17 sequence. Differences in sequence between L17 and KIF-2 are shown, with the differing KIF-2 bases printed above the L17 sequence. Positions −493, −21, +1, and 624 of the KIF-2 sequence are indicated.

FIG. 8 depicts a diagram and sequence of Src SH3 binding cDNA L35. Position 1 is the first base of the insert sequence after the EcoRI site of the vector, position 261 is the last base of the insert before the HindIII site of the vector. Three consecutive translation stop codons are located at nucleotides 88–96. The putatative SH3 binding domain (L35) is indicated by a bar on the diagram and the sequence of the synthesized peptide L35 is underlined below. Clone L35 contained a cDNA insert of only 261 bp possessing an open reading frame of 30 amino acids, in which a proline-rich putative SH3-binding sequence was found (FIG. 8). The size of the encoded polypeptide (approximately 3.3 kDa) is in good agreement with that predicted (3–5 kDa) from the migration of the L35 fusion protein (FIG. 5a), after subtraction of the mass of the T7 gene 10 protein sequences. The cDNA and deduced amino acid sequences of clone 35 show no significant homology to any sequences in the current nucleic acid and protein databases.

C. Truncations of cDNAs

Truncated versions of L14 and L17 clones were prepared as follows: Lambda 14 was digested with HindIII (internal site at nt 532) and the fragment containing the vector plus the 5' portion of the insert cDNA was gel purified and recircularized by ligation. This construct (DL14) consisted of only the 178 amino-terminal amino acid residues of L14 and contained only one putative SH3 binding domain (FIG. 6). The extreme 5' portion of L17 was prepared by digesting the clone with SmaI and HindIII (SmaI site at nt 85 of insert and HindIII site at nt 987) which releases the majority of the cDNA insert leaving only the sequence encoding the proline-rich amino-terminal 28 residues. After gel purification, the vector and extreme 5' portion of L17 was recircularized by ligation at the blunted HindIII and SmaI sites. Truncated versions were used for Northern blotting analysis, or expressed and analyzed in the binding assay described below.

D. Analysis of SH3 domain binding by clones L14, L17, and L35

A panel of SH3 domains from various proteins (c-src kinase, neuronal src, fgr-kinase, pl 3-kinase p85a subunit, NCF1/2 and NCF2/2) produced as GST fusions in recombinant pGEX vectors was kindly provided by Dr. Ivan Gout, Ludwig Institute for Cancer Research, London; pGEX vectors encoding GST/rasGAP and GST/Grb2 SH3 domains were provided by Dr. Bruno Tocqué, Rhône-Poulenc Rorer, Vitry sur Seine, France; cDNA encoding the SH3 domains of fyn-kinase, csk-kinase, PLC-g and crk-protooncogene were produced by reverse-transcriptase-PCR and cloned into pGEX-2T vector between the BamHI and EcoRI sites. All GST/SH3 fusions were expressed and purified using glutathione-Sepharose affinity chromatography as described above. These GST/SH3 fusions were reacted with NC membranes containing the expressed T7 gene 10 cDNA fusions using the same binding conditions as used for library screening. Binding reactivity was detected with an anti GST antibody (Amrad, Australia) diluted 1:5000 followed by anti rabbit IgG-HRP (1:2000 dilution; Boehringer) and ECL methodology (Amersham). The results of these analyses are shown in FIG. 9 and summarized in Table 2.

FIG. 9 demonstrates the reaction of electroblotted Src SH3 binding protein-gene 10 fusions with a panel of various SH3/GST fusion proteins. Inductions of the Src SH3 binding protein-gene 10 fusions from pEXlox clones (L35, L17, DL14, and L14) were run on SDS PAGE gels and transferred to nitrocellulose. Blots were reacted with various GST/SH3 fusions or GST only as indicated. The origin of the SH3 domain in each GST fusion is indicated in parenthesis. The GST/Src SH3 fusions also contained the Protein Kinase A (PKA) labeling site, and in the first panel the site has been phosphorylated with nonradioactive ATP by PKA. The reaction of GST/SH3 fusions with the blotted SH3-binding protein-gene 10 fusions was detected using a rabbit polyclonal anti GST antibody (Amrad), followed by an anti Rabbit IgG-HRP conjugate antibody, with subsequent ECL (enhanced chemiluminesence) reaction and exposure to X-ray film. Mobility of MW markers are indicated. DL14 is a truncated version of L14, containing only the $NH_2$ terminal SH3-binding sequence.

L35 reacted most strongly with the SH3 domains of c-src (FIG. 9b) and c-fyn (not shown), and to lesser degrees with other SH3 domains, such as c-fgr (FIG. 9c) and Grb2 amino-terminal (FIG. 9d) and carboxyl-terminal (FIG. 9i) SH3 domains. In general, L35 bound better and to a greater variety of SH3 domains than did L14 and L17, but was unable to bind to several SH3 domains, such as rasGAP (FIG. 9g) and bound some others very poorly. Table 2 summarizes the binding experiment data presented in FIG. 9. The relative strength of binding is shown as indicated.

TABLE 2

| Analysis of SH3 Domain binding specificity | | | |
|---|---|---|---|
| SH3 domain | L14 | L17 | L35 |
| c-src | +++ | +−(+++)* | ++++ |
| neuronal src | +− | − | ++ |
| c-Fyn | ++++ | +− | ++++ |
| fgr | +++ | +− | +++ |
| CRK | − | − | + |
| PLC-g | −(++**) | − | ++ |
| H-NCF 1/2 | − | − | +− |
| H-NCF 2/2 | − | − | − |
| GRB-2 N term | + | +− | ++ |
| GRB-2 C term | − | +− | ++ |
| GRB-2 Full length | +− | +− | ++ |
| GAP | − | + | − |
| PI 3-kinase p85a | ++ | + | ++ |
| R-CSK | − | − | − |

(−) no detectable interaction by all methods;
(+−) very weak binding;
(+) weak binding but easily detected by all methods;
(++) moderate binding;
(+++) strong and
(++++) very strong binding.
*binding only with phosphorylated GST/PKA/Src SH3
**Binding only wkh peptide immobilized on AminoLink ® agarose L14 reacted with many but not all of the SH3 domains which reacted with L35. Strongest reactions were observed with the SH3 domains of c-src (FIG. 9b), c-fgr (FIG. 9c) and c-fyn (not shown). L14 reacted less well with other SH3 domains, such as Grb2 amino-terminal (FIG. 9d) and PI 3-kinase p85a subunit (FIG. 9f) and didn't react with others such as Grb2 carboxyl-terminal (FIG. 9i) and rasGAP (FIG. 9g) SH3 domains. Unlike L35, only the amino terminal but not the carboxyl terminal Grb2 SH3 domain bound to L14. The DL14 and full length L14 proteins bound equally well and to the same spectrum of SH3 domains (FIG. 9), suggesting that the amino terminal putative SH3 binding domain (residues 21–29) is the main SH3 binding site within the L14 protein.

In general, L17 bound much less well to the same spectrum of SH3 domains than did L35 or L14, with the notable exception of rasGAP (FIG. 9g), to which only L17 bound weakly and neither L35 nor L14 bound. The reaction of L17 was most strong with the SH3 domains of PI 3-kinase p85a (FIG. 9f) and rasGAP (FIG. 9g). Surprisingly, in this experiment L17 failed to react with the SH3 domain of c-src (FIG. 9a), although L17 was cloned on this basis and bound to the $^{32}$P-GST/PKNSrc SH3 probe but not to the control $^{32}$P-GST/PKA probe (FIGS. 5a,b). The main difference between the experiments presented in FIG. 5 and FIG. 9 is the method of detection of the bound SH3 domains: in FIG. 5 the GST/PKNSrc SH3 fusion protein was phosphorylated in vitro with $^{32}$P-g-ATP and detected by autoradiography, whereas in FIG. 9 bound GST/SH3 fusion proteins were detected with anti GST antibodies followed by ECL. These results suggested that serine phosphorylation of the PKA recognition site within the GST/PKNSrc SH3 fusion protein was crucial for the binding of of the src SH3 sequence to the L17 protein. To test this possibility, the GST/PKNSrc SH3 fusion protein was phosphorylated in vitro with non-radioactive ATP, reacted with filters containing the L14, L17 and L35 proteins, and detected with anti-GST antibodies and ECL. Indeed, the presence of the phosphorylated serine in the c-srcSH3 domain's amino terminal flanking sequence was crucial for the binding to the L17 fusion protein (FIGS. 9a,b,e). A fusion protein in which the PKA recognition site was situated downstream of the c-srcSH3 domain and phosphorylated in vitro with $^{32}$P-γ-ATP was unable to bind L17, but bound to L35 and L14 like the original $^{32}$P-GST/PKNSrc SH3 probe (data not shown). These results argue that it is not the phosphorylated PKA site within the GST/PKNSrc SH3 fusion protein per se which is responsible for the interaction with L17. Rather, these results demonstrate that serine phosphorylation within the flanking sequence amino terminal to the c-srcSH3 domain is necessary for the recognition of L17 by the GST/PKNSrc SH3 fusion protein. Consistent with these findings, only L14 and L35 proteins but not L17 were able to bind to full length autophosphorylated c-src kinase in vitro. It is uncertain whether in vivo the affinity or specificity of binding of the c-srcSH3 domain is similarly regulated by upstream serine/threonine phosphorylation. This may also be applicable for the SH3 binding motifs. In such cases, phosphorylation-dephosphorylation may potentially serve as an important regulator of SH3 domain binding. The importance of serine/threonine phosphorylation in controlling the growth factor activated MAP kinase pathway was demonstrated recently (49, 50). In these experiments, the association of raf-1 kinase with p21 ras was inhibited by phosphorylation of raf-1 on serine 43 by the cAMP-dependent protein kinase, PKA. In a similar manner, cAMP-elevating agents which activate PKA may potentially regulate interactions between SH3 domains and SH3 binding proteins. We have found that the SH3-binding protein L14 can be phosphorylated by src kinase in vitro, and several candidate tyrosine phosphorylation sites are indicated in the L14 sequence (FIG. 6). In this respect, L14 protein resembles actin filament-associated protein AFAP-110 which has srcSH3 binding sites (FIG. 10) and is tyrosine phosphorylated by src kinase (51). Whether or not this phosphorylation is physiologically important is unclear.

E. Identification of SH3-binding sequences within clones L14, L17, and L35.

As mentioned above, putative SH3-binding sequences in clones L14, L17, and L35 were tentatively identified based on their proline-rich character (FIGS. 5–8). An alignment of these putative sequences with the some of known SH3-binding sequences in different proteins is shown in FIG. 10. The possible alignments of some SH3 binding motifs from various proteins is also shown.

This analysis showed that the sequence of this region of clone L35 (residues 13–24, FIG. 8), which exhibited the best binding to the greatest variety of tested SH3 domains, contains a hexapeptide sequence PPPΨPP (SEQ ID NO: 38) (where Ψ is hydrophobic amino acid) which is also found in the SH3-binding domains of 3BP-1, formin and mSOS. Of the two candidate SH3-binding sequences in clone L14 (residues 19–30 and residues 246–253, FIG. 6) only the amino-terminal motif could be reasonably aligned with the known SH3-binding sequences. This motif bears a striking resemblance to the heptamer consensus sequence identified by screening of the phage random peptide library with the SH3 domain of c-src (Table 1). The amino terminal putative SH3-binding motif in clone 17 (L17-1, residues 30–43, FIG. 7) has ~46% identity with the P2 sequence within dynamin (FIG. 10) and ~60% amino acid homology with P1 sequence from dynamin (the P1 proline-rich sequence, residues 785–806 of dynamin p100 overlaps with the P2 sequence, residues 777–794, see ref. 22). In spite of having 10 common residues, the P1 and P2 dynamin sequences displayed very different SH3 binding properties; while the P2 sequence had the same SH3 binding specificity (including binding of c-src SH3) as native dynamin, a synthetic peptide corresponding to the P1 sequence inhibited the association of dynamin with the SH3 domains of PI 3-kinase p85a and PLC-g but didn't bind c-src SH3 (22). This is consistent with the data presented in FIG. 9 and Table 2 in which L17 bound best to the PI 3-kinase p85a SH3 domain. The carboxyl terminal putative SH3-binding motif in clone 17 (residues 72–88, FIG. 6) resembles the upstream motif but aligned less well to the P2 (and P1 motif, not shown) sequence of dynamin (FIG. 10). In general, the proline-rich sequences in clone L17 have poor homology with other SH3 binding motifs presented in FIG. 10.

In order to determine whether the putative SH3 binding motifs in clones L14, L17, and L35 can bind to the SH3 domains of c-src and other proteins, 5 synthetic peptides were prepared: Peptides corresponding to putative SH3 binding domains were synthesized as described in Example 1 and coupled to 500 ml of AminoLink® agarose (Pierce). The peptides had the following sequences: pL14-1: QSRPLPSPPKFT (SEQ ID NO: 18; L14 residues 18–29, FIG. 6); pL14-17mer: RPLPSPP (SEQ ID NO: 35, L14 residues 20–26, FIG. 6); pL14-2: PQHSAVPPRPGPA (SEQ ID NO: 39, L14 residues 241–253, FIG. 6); pL17-1: AHPPARPPVRPQPG (SEQ ID NO: 20, L17 residues 30–43, FIG. 7); pL17-2: APPAATPPPPRLFRPPA (SEQ ID NO: 21, L17 residues 72–88, FIG. 7); pL35: TPAPPPLPPRNV (SEQ ID NO: 17, L35 residues 13–24, FIG. 8); pSV40: KPPTPPPEPET (SEQ ID NO: 22, Sigma L0765). The coupled peptides were reacted with radiolabeled GST/PKNSrc SH3, GST/PKNrasGAP SH3 or GST/PKA (control) fusions ($8 \times 10^5$ dpm) or with unlabeled GST/SH3 fusions (5 μg). The binding was done at room temperature for 1 hour and the resin was washed extensively with TTBS. Binding of radiolabeled probes was determined in a scintillation counter. Unlabeled GST/SH3 fusions were released from resin by boiling in SDS sample buffer and analyzed by SDS-PAGE. Relative binding was expressed as a % of input cpm for radiolabeled fusions or by the relative intensity of the Coomassie blue-stainable band for unlabeled fusions. Controls included labeled (GST/PKA) and unlabeled GST alone with each of the peptides and reaction of SH3 fusions with a heterologous proline-rich peptide from SV40 T antigen.

Figures 11A, 11B:
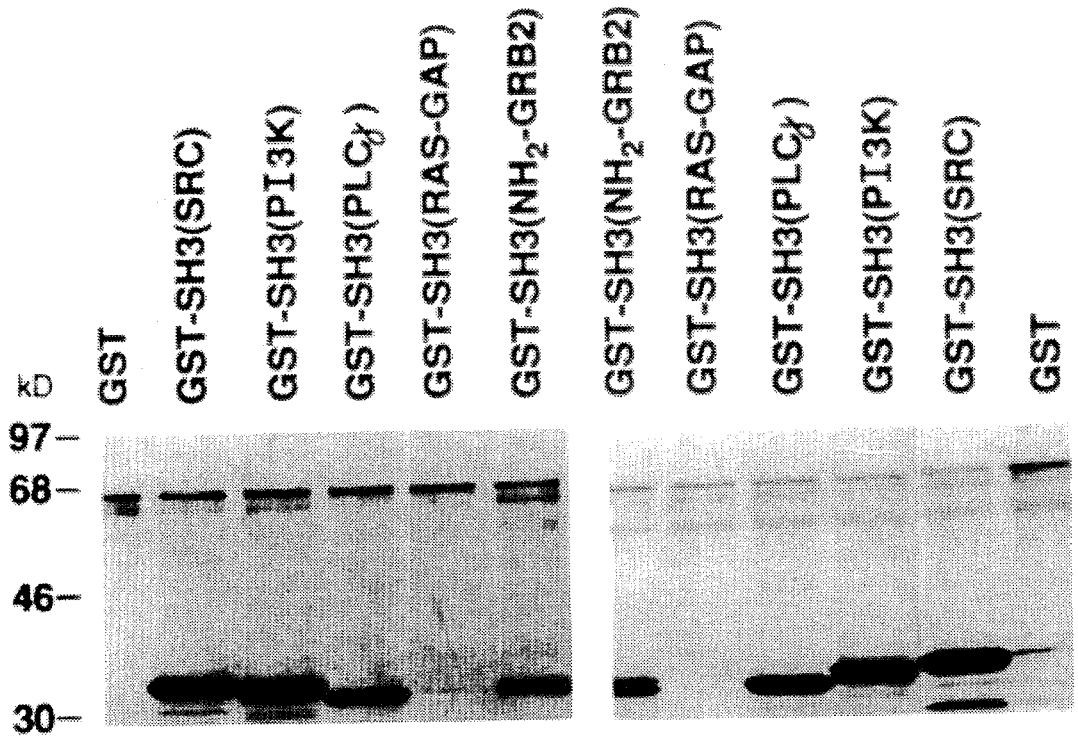
FIG. 11 demonstrates the binding analysis of peptides representing putative SH3 binding sites of the cloned proteins L14, L17 and L35 with various SH3 domains.
Figures 11C, 11D:
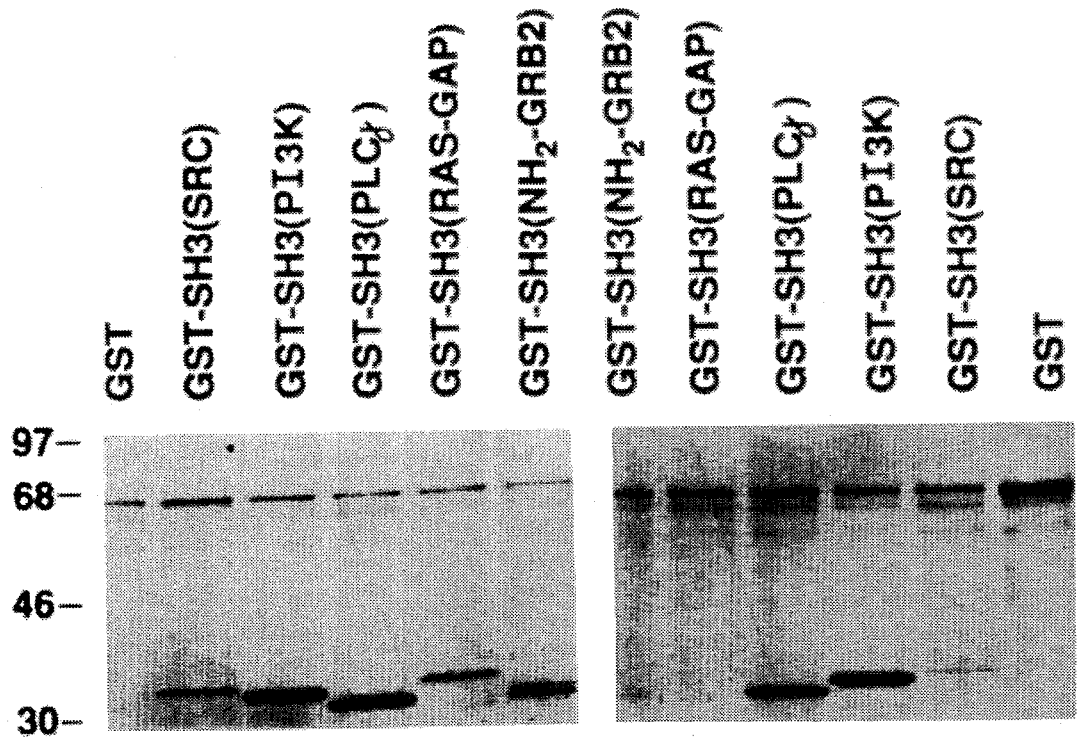

FIG. 11 demonstrates the binding analysis of peptides representing putative SH3 binding sites of the cloned proteins L14, L17 and L35 with various SH3 domains.

Peptides (L14-1, L35, L17-1, and L17-2) corresponding to the putative SH3 binding domains of the pEXlox clones (L14, L35, and L17) were coupled to Aminolink® agarose. The bound peptides were then reacted with equal amounts of various purified GST/SH3 fusions or with purified GST alone. The peptide-linked agarose beads were thoroughly washed and then resuspended in SDS loading dye, boiled and run on SDS-PAGE gels along with MW size markers. The gels were stained with Coomassie blue and the presence and intensity of the captured GST/SH3 fusion protein was ascertained. The 69 kD band seen in all lanes is bovine serum albumin, which was used to block nonspecific binding sites on beads and was included in the reaction buffer (3%), as well. On FIG. 11: Gel A. reacted with peptide pL14-1; B. reacted with peptide pL35; C. reacted with peptide pL17-2, and D. reacted with peptide pL17-1. The panel of GST fusions reacting with the coupled peptides is indicated above the corresponding lanes of the gels. Mobilities of MW markers (size in kD) are indicated.

Figure 12:
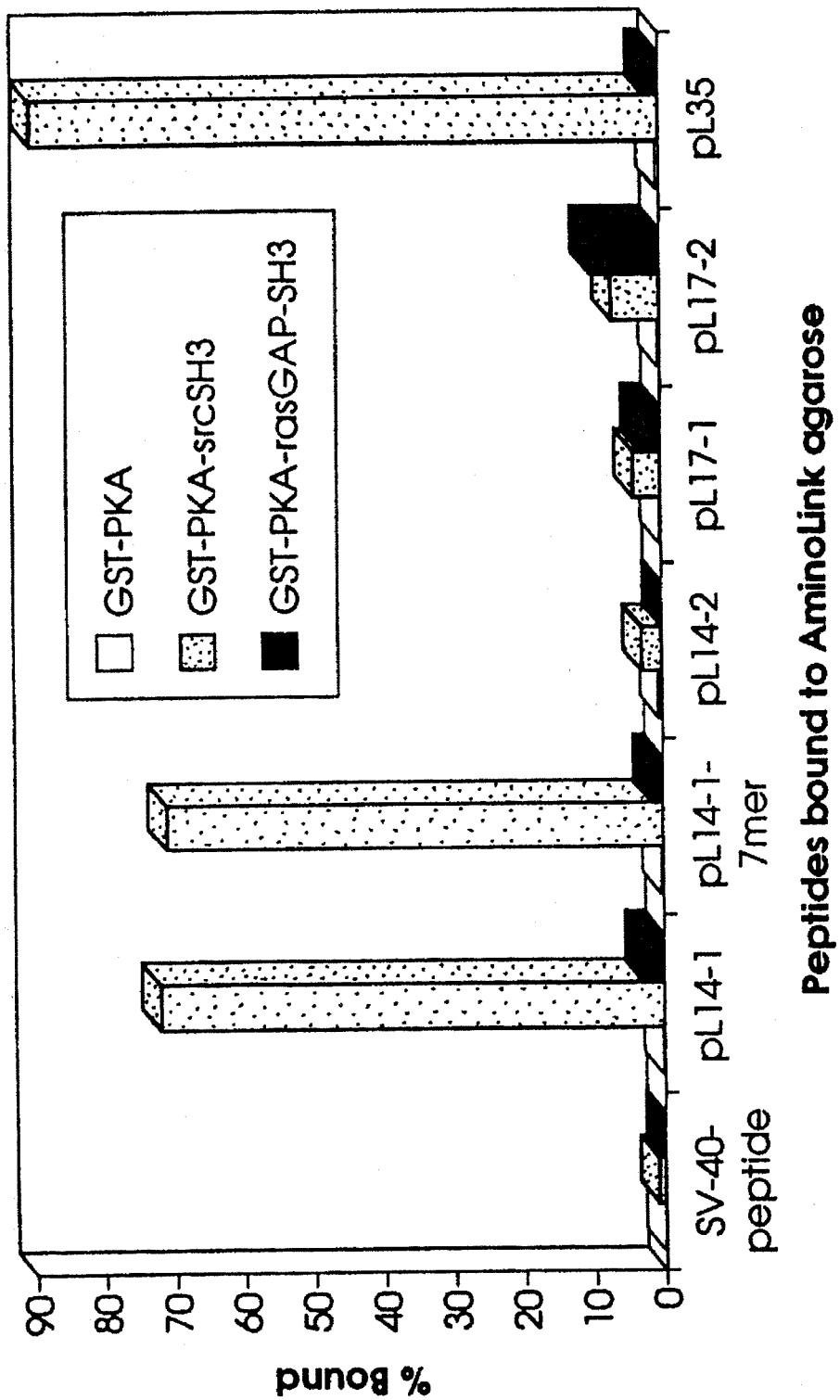
FIG. 12 demonstrates the binding of radiolabeled $^{32}$P-GST/PKNSH3 fusions to immobilized peptides.

FIG. 12 demonstrates the binding of radiolabeled $^{32}$P-GST/PKA/SH3 fusions to immobilized peptides. Peptides representing putative SH3 binding motifs determined from the sequences of clones L14, L17, and L35 were coupled to Aminolink® agerose, as described for FIG. 11. As a control a proline rich peptide from SV40 T antigen was also coupled. Peptide-linked beads were reacted with $^{32}$P-GST/PKNSH3 domains from c-src and rasGAP proteins and to $^{32}$P-GST/PKA alone, washed extensively with TTBS and the binding of radiolabeled proteins determined by scintillation counting. The bar graph shows the amount of labeled fusion bound to each peptide-linked resin as a % of total input cpm.

In this analysis no binding of any of the peptides to the negative control GST protein (FIG. 11) nor any binding of SH3 domains to the negative control SV40 peptide (FIG. 12) was observed. Peptides pL14-1 and pL35 (FIGS. 11a,b) bound well to the SH3 domains of PI 3-kinase p85a subunit and c-src and not to rasGAP, as expected from the results with the L14 and L35 fusion proteins (FIGS. 9a,b,f,g, Table 2). The SH3 domain of PLC-g also bound well to peptide pL14-1, which contrasts with the results obtained with the L14 fusion protein (FIG. 9j, Table 2). The SH3 binding motifs from both L35 and L14 proteins have a flanking Arg residue at the carboxyl terminus of the L35 SH3 binding motif (PPPLPPR, SEQ ID NO: 40) and at the amino terminus of the L14 SH3 binding motif (RPLPSPP, SEQ ID NO: 35). The specific binding of SH3 domains by these proline-rich motifs may depend partially on the presence of a flanking arginine. The importance of carboxyl Arg in SOS proline-rich motifs for the binding of Grb2 SH3 domains has been previously described (9).

Peptide p17-1 (FIG. 11d) bound poorly to the c-src SH3 domain but bound well to the SH3 domain of PI 3-kinase p85a, as expected from the binding of the L17 fusion protein with GST/p85a SH3 (FIG. 9f, Table 2). Similar to the results obtained with peptide pL14-1, the peptide pL17-1 bound comparatively well to GST/PLC-g SH3, despite the inability of the L17 fusion protein to bind to GST/PLC-g SH3 (FIG. 9j, Table 2). The discrepencies between the results of FIGS. 9 and 11 may be due to the use of reduced, denatured and electroblotted T7 gene 10 protein fusions in FIG. 9 vs. immobilized peptides in FIG. 11. Alternatively, the discrepencies may indicate that sequences which flank the SH3 binding domains in L14 and L17 proteins (but not in L35) exert a negative influence on its binding to some (eg. PLC-g SH3 domain) but not all SH3 domains. This negative effect would not be observed in the experiments described in FIGS. 11 and 12 which utilized short, synthetic peptides.

Peptide L17-2 behaved identically to peptide L17-1 with respect to its binding to the SH3 domains of PI 3-kinase p85a, c-src, and PLC-g. However, in contrast to the other peptides, only peptide L17-2 displayed any binding to the SH3 domain of rasGAP (FIG. 11c), consistent with the observed binding of GST/rasGAP SH3 to electroblotted L17 but not L14 or L35 fusion proteins (FIG. 9g, Table 2). The recognition of rasGAP SH3 by peptide L17-2, although weak, reflects a specific but probably sub-optimal interaction. This is not surprising in view of the fact that clone L17 was isolated on the basis of its binding to the SH3 domain of c-src, which is quite different from the SH3 domain of rasGAP protein (4).

The experiments shown in FIG. 11 demonstrate that the putative SH3 binding motifs identified in clones L14, L17 and L35 bind to the SH3 domains of several different proteins to varying extents. The results also show that a given SH3 domain-containing protein recognizes divergent SH3 binding motifs to different degrees.

In an attempt to quantitate the relative binding of different SH3 domains to the SH3 binding motifs identified in clones L14, L17 and L35, GST/PKNSH3 fusion proteins (or, as control, GST/PKA) were phosphorylated in vitro with $^{32}$P-$\gamma$-ATP and reacted with the peptide-linked beads as described in FIG. 11. After removal of unbound proteins by extensive washing, bound CPM was measured in a $\beta$-counter. Binding was expressed as percent of CPM bound to beads/CPM applied to beads. An additional control in this experiment consisted of beads linked to a proline-rich peptide derived from the COOH terminus of SV40 T antigen. This peptide, KPPTPPPEPET (SEQ ID NO: 22), somewhat resembles a consensus SH3 binding motif (FIG. 10). Peptides pL14-1 and pL35 both efficiently bound (70 and 90%, respectively) to the SH3 domain of c-src, as expected from previous results (FIGS. 5, 9, and 11). Peptide pL14-1-7-mer, a truncated version of peptide pL14-1, bound to the SH3 domain of c-src with the same efficiency (FIG. 12). The binding of peptides pL14-2, pL17-1 and pL17-2 to the SH3 domain of c-src was quite low by comparision (5–10%) but significantly higher than that obtained (<1%) with the SV40 peptide. These results are consistent with the poor alignment of pL14-2, pL17-1 and pL 17-2 to SH3-binding consensus sequences (FIG. 10). The best binding to the rasGAP SH3 domain, ~10%, was observed with peptide pL17-2. This result compares favorably to those in FIG. 11, showing low but approximately equal binding of c-src and rasGAP SH3 domains to peptide p17-2.

Ren and colleagues localized the c-abl SH3 binding motifs of two proteins, 3BP-1 and 3BP-2, to a ten or nine amino acid stretch with the overall consensus of XPXXPPPΨXP (20). The SH3 binding motif L35 conforms best to this motif, with the exception that proline is in the third rather than the second position. Since L35 is unable to bind c-abl SH3 domain (M.Duschesne, personal communication), it would appear that proline in position 2 is obligatory for binding to SH3 domain of c-Abl but not for the binding to the SH3 domains from several other proteins (eg., c-Src, c-Fyn, PI 3-kinase p85a). Peptide pL14-1 diverges even further from the decamer consensus sequence, yet is capable of binding a variety of SH3 domains, as are peptides pL17-1 and pL17-2, which are even more divergent. Peptide pL17-1 and, to a lesser degree, pL17-2, bears significant homology to a promiscuous SH3 binding motif in the GTPase dynamin which bears little resemblance to the decamer consensus sequence. These data indicate that key proline residues are essential for SH3 binding, but surrounding residues influence binding, and caution that it may be oversimplistic to attempt to determine general SH3-binding consensus sequences. It is interesting that only the most divergent SH3 binding motif, pL17-2, displayed any binding (albeit weak) to the rasGAP SH3 domain. This result suggests that families of SH3 binding motifs will likely be identified, and that it is quite unlikely that rasGAP SH3 binding motifs will bear much resemblance to the decamer SH3 binding consensus sequence already described.

E. mRNA analysis

A multiple tissue Northern blot containing mRNAs from various tissues of adult mice and rats was used to examine the size(s) and tissue distribution of mRNAs hybridizing to radiolabelled cDNA probes of clones L14, L17, and L35. $^{32}$P cRNA probes were made from each of the isolates, the truncated version of L17, as well as a PCR produced fragment of L17 which contained only the KIF-2 domain. The cRNA runoffs were prepared using SP6 RNA polymerase and the SP6 promoter sequence located 3' of the cDNA cloning site in pEXlox. The probes that were generated were used to hybridize to a Northern blot containing mouse mRNA (2 μg/lane) from various tissues (MTN Clonetech). The blot was prepared, hybridized and stripped according to the manufacturer's instructions. The results of this analysis are summarized in Table 3. Clone L14 detected a ~1.5 kb mRNA which is most highly expressed in heart and skeletal muscle. The lack of detection of this mRNA in brain is surprising, since clone L14 appears to be the mouse homologue of EST06380, which was cloned from a human infant brain cDNA library (47). This result suggests that expression of this gene in the brain may be developmentally regulated.

TABLE 3

General characteristics of clones L14, L17, and L35 cDNA inserts, encoded open reading frames, and tissue distribution of mRNA.

|  | Lambda 14 | Lambda 17 | Lambda 35 |
| --- | --- | --- | --- |
| cDNA size | 1168 bp | 987 bp | 261 bp |
| ORF size | 370 aa | 329 aa | 30 aa |
| Predicted MW of protein | 40.1 kD | 35.99 kD | 3.2 kD |
| Observed MW of protein | 40 kD | 48 kD | 3.0 kD |
| Homology | human brain cDNA[4] | mouse KIF-2 protein[5] | no significant homology detected |
| mRNA size (kb) | 1.5 | 4.5[1], 3.5[2], 3.0 | 4.0 |
| Tissue distribution[3] | H*, SM | H, Br*, Sp, Liv, SM, K, | H, Br*, Sp, Liv, SM, K, |

*The asterisk indicates tissue showing the strongest signal.
[1]indicates the only mRNA size detected using the non KIF-2 portion of L17 as a probe.
[2]indicates the strongest hybridizing mRNA seen when the entire L17 cDNA insert was used as a probe.
[3]tissue type, Br — brain, H — heart, K — kidney, Liv — liver, Sp — spleen, SM — skeletal muscle, T — testes.
[4]Adams, M., Soares, M. Kerlavage, A., Fields, C., Venter, J. C. (1993) Nature genetics 4, 373–380.
[5]Aizawa, H., Sekine, Y., Takemura, R., Zhang, Z., Nangaku, M., and Hirokawa, N. (1992) Journal of Cell Biology 119, 1287–1296.

The complete, 987 bp probe of L17 detected mRNAs of 4.5, 3.5, and 3.0 kb, as previously reported for the mouse kinesin-like protein KIF-2 (48). The greatest expression of these mRNAs was found in brain, with weaker expression in spleen and heart. A probe derived from the 253 bp sequence in L17 which is not contained within the KIF-2 sequence hybridized only to the 4.5 kb mRNA. As this region of L17 contains functional SH3-binding domains, the differential expression of these KIF-2 mRNAs may have important functional significance. Clone L17 may represent a developmentally important form of kinesin which might be regulated by specific interaction with PI 3-kinase, src-kinase, or other SH3 domain-containing proteins. It is possible, for example, that src, through its SH3 domain, may bind to the proline rich motifs identified in the L17 protein, and either regulate the activity or cellular distribution of this KIF-2 variant. The importance of appropriate regulation of src activity for the proper development of the nervous system (52) may, in part, be related to this interaction.

Since L17 appears to be an alternatively spliced form of KIF-2 capable of interaction with various SH3 domains, it may represent a developmentally important form of kinesin which might be regulated by specific interaction with PI 3-kinase, src-kinase, or other SH3 domain-containing proteins.

The probe made from the L35 cDNA insert hybridized to a 4.0 kb mRNA which is most highly expressed in brain, with lesser expression observed in various other tissues.

Altogether, the results of the mRNA analysis indicate that L14, L17, and L35 represent partial cDNA clones, with different patterns of tissue-specific expression.

The non-receptor tyrosine kinase c-src represents the prototypic member of a family of cytoplasmic tyrosine kinases which are involved in signal transduction cascades initiated in various ways, including activation of cytokine or growth factor receptors as well as activation of T-cells and platelets. C-src consists of an SH3, SH2 and tyrosine kinase domain, and each of these modules (SH3, SH2, and tyrosine kinase domain) are present in a variety of cellular proteins which perform a myriad of functions. In this invention, 3 cDNA clones encoding proteins which interact with the SH3 domain of c-src are described, as well as the amino acid sequences which mediate this binding. Based on these results, it is obvious that screening of other cDNA libraries with the c-src SH3 domain or with the SH3 domains of other proteins will result in the identification of other SH3-binding proteins and the elucidation of sequences which mediate binding in these cases. Furthermore, this invention also describes a novel heptamer amino acid motif identified by screening a phage random peptide library with the SH3 domain of c-src. The identification of additional binding motifs for specific SH3 domains by further application of the phage peptide library approach is now predictable.

One skilled in the art will readily appreciate the present invention is well adapted to carry out the objects and obtain the ends and advantages mentioned, as well as those inherent therein. The peptides, nucleotides encoding them, methods, procedures and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

All patents and publications mentioned in this specification are indicative of the level of those skilled in the art to which the invention pertains. All patents and publications are herein incorporated by reference to the same extent as if each individual publication was specifically and individually indicated to be incorporated by reference.

REFERENCES

1. Cantley, L. C., Auger, K. R., Carpenter, C., Duckworth, B., Graziani, A., Kapeller, R., Soltoff, S. (1991) *Cell* 64, 281–302
2. Koch, C. A., Anderson, D., Moran, M. F., Ellis, C., Pawson, T. (1991) *Science* 252, 668–74
3. Mayer, B. J., Hamaguchi, M., Hanafusa, H. (1988) *Nature* 332, 272–275
4. Musacchio, A., Gibson, T., Lehto, V. P., Saraste, M. (1992) *Febs Lett* 307, 55–61
5. Clark, S. G., Stern, M. J., Horvitz, H. R. (1992) *Nature* 356, 340–4
6. Lowenstein, E. J., Daly, R. J., Batzer, A. G., Li, W., Margolis, B., Lammers, R., Ullrich, A., Skolnik, E. Y., Bar-Sagi, D., Schlessinger, J. (1992) *Cell* 70, 431–42
7. Chardin, P., Camonis, J. H., Gale, N. W., van Aelst, L., Schlessinger, J., Wigler, M. H., Bar-Sagi, D. (1993) *Science* 260, 1338–43
8. Olivier, J. P., Raabe, T., Henkemeyer, M., Dickson, B., Mbamalu, G., Margolis, B., Schlessinger, J., Hafen, E., Pawson, T. (1993) *Cell* 73, 179–91

9. Rozakis-Adcock, M., Fernley, R., Wade, J., Pawson, T., Bowtell, D. (1993) *Nature* 363, 83–5
10. Soriano, P., Montgomery, C., Geske, R., Bradley, A. (1991) *Cell* 64, 693–702
11. Okada, M., Howell, B. W., Broome, M. A., Cooper, J. A. (1993) *J Biol Chem* 268, 18070–5
12. Superti-Furga, G., Fumagalli, S., Koegl, M., Courtneidge, S. A., Draetta, G. (1993) *Embo J* 12, 2625–34
13. Dezelee, P., Barnier, J. V., Hampe, A., Laugier, D., Marx, M., Galibert, F., Calothy, G. (1992) *Virology* 189, 556–67
14. Weng, Z., Taylor, J. A., Turner, C. E., Brugge, J. S., Seidel-Dugan, C. (1993) *J Biol Chem* 268, 14956–63
15. Anderson, D., Koch, C. A., Grey, L., Ellis, C., Moran, M. F., Pawson, T. (1990) *Science* 250, 979–982
16. Fantl, W. J., Escobedo, J. A., Martin, G. A., Turck, C. W., del Rosario, M., McCormick, F., Williams, L. T. (1992) *Cell* 69, 413–23
17. Waksman, G., Kominos, D., Robertson, S. C., Pant, N., Baltimore, D., Birge, R. B., Cowburn, D., Hanafusa, H., Mayer, B. J., Overduin, M., et, al (1992) *Nature* 358, 646–53
18. Zhou, S., Shoelson, S. E., Chaudhuri, M., Gish, G., Pawson, T., Haser, W. G., King, F., Roberts, T., Ratnofsky, S., Lechleider, R. J., et al. (1993) *Cell* 72, 767–78
19. Cicchetti, P., Mayer, B. J., Thiel, G., Baltimore, D. (1992) *Science* 257, 803–6
20. Ren, R., Mayer, B. J., Cicchetti, P., Baltimore, D. (1993) *Science* 259, 1157–61
21. Prasad, K. V., Janssen, O., Kapeller, R., Raab, M., Cantley, L. C., Rudd, C. E. (1993) *Proc Natl Acad Sci U.S.A.* 90, 7366–70
22. Gout, I., Dhand, R., Hiles, I. D., Fry, M. J., Panayotou, G., Das, P., Truong, O., Totty, N. F., Hsuan, J., Booker, G. W., et al. (1993) *Cell* 75, 25–36
23. Geysen, H. M., Rodda, S. J., Mason, T. J., Tribbick, G., Shoofs, P. G. (1987) *J. Immunol. Methods* 102, 259–274
24. Fodor, S. P. A., Read, J. L., Pirrung, M. C., Stryer, L., Lu, A. T., Solas, D. (1991) *Science* 251, 767–772
25. Lam, K. S., Salmon, S. E., Hersh, E. M., Hruby, V. J., Kazmierski, W. M., Knapp, R. J. (1991) *Nature* 354, 82–84
26. Houghten, R. A., Pinella, C., Blondelie, S. E., Appel, J. R., Dooley, C. T., Cuervo, J. H. (1991) *Nature* 354, 84–86
27. Scott, J. K., Smith, G. P. (1990) *Science* 249, 386–90
28. Houghten, R. A., Appel, J. R., Blondelie, S. E., Cuervo, J. H., Dooley, C. T., Pinilia, C. (1992) *Bio Techniques* 13, 412–421
29. Cwirla, S. E., Peters, E. A., Barrett, R. W., Dower, W. J. (1990) *Proceedings of the National Academy of Sciences* 87, 6378–6382
30. Felici, F., Castagnoli, L., Musacchio, A., Japelli, R., Cesareni, G. (1991) *J. Mol. Biol.* 222, 301–310
31. Stephen, C. W., Lane, D. P. (1992) *J. Mol. Biol.* 225, 577–583
32. Lenstra, J. A., Erkens, J. H. F., Langeveld, J. G. A., Posthumus, W. P. A., Meloen, R. H., Gebauer, F., Correa, I., Enjuanes, L., Stanley, K. K. (1992) *J. Immunol. Methods* 152, 149–157
33. Luzzago, A., Felici, F., Tramontano, A., Pessi, A., Cortese, R. (1993) *Gene* 128, 51–57
34. Blond-Elguindi, S., Cwirla, S. E., Dower, W. J., Lipshutz, R.-J., Sprang, S. R., Sambrook, J. F., Gething, M.-J. H. (1993) *Cell* 75, 717–728
35. Dedman, J. R., Kaetzel, M. A., Chan, H. C., Nelson, D. J., Jamieson, G. A.
36. Koivunen, E., Gay, D. A., Ruoslahti, E. (1993) *The Journal of Biological Chemistry* 268, 20205–20210
37. O'Neil, K. T., Hoess, R. H., Jackson, S. A., Ramachandran, N. S., Mousa, S. A., DeGrado, W. F. (1992) *Proteins: Structure, Function, and Genetics* 14, 509 515
38. Smith, G. P., Schultz, D. A., Ladbury, J. E. (1993) *Gene* 128, 37–42
39. Devlin, J. J., Panganiban, L. C., Devlin, P. E. (1990) *Science* 249, 404–6
40. Scott, J. K., Loganathan, D., Easley, R. B., Gong, X., Goldstein, I. J. (1992) *Proc. Natl. Acad. Sci. U.S.A.* 89, 5398–5402
41. Oldenburg, K. R., Loganathan, D., Goldstein, I. J., Schultz, P. G., Gallop, M. A. (1992) *Proc. Natl. Acad. Sci. U.S.A.* 89, 5393–5397
42. Chen, J. K., Lane, W. S., Brauer, A. W., Tanaka, A., Schreiber, S. L. (1993) *Journal of the American Chemical Society* 115, 12591–12592
43. Ron, D., Dressier, H. (1992) *BioTechniques* 13, 866–869
44. Parmley, S. F., Smith, G. P. (1988) *Gene* 73, 305–318
45. Fields, C. G., Lloyd, D. H., MacDonald, R. L., Otteson, K. M., Noble, R. L. (1991) *Peptide Research* 4, 95–101
46. King, D. S., Fields, C. G., Fields, G. B. (1990) *International Journal of Peptide and Protein Research* 36, 255–266
47. Adams, M., Soares, M., Kerlavage, A., Fields, C., Venter, J. C. (1993) *Nature genetics* 4, 373–380
48. Aizawa, H., Sekine, Y., Takemura, R., Zhang, Z., Nangaku, M., and Hirokawa, N. (1992) *Journal of Cell Biology* 119, 1287–1296
49. Cook, S., McCormick, F. (1993) *Science* 262, 1069–1072
50. Wu, J., Dent, P., Jelinek, T., Wolfman, A., Weber, M., Sturgill, T. (1993) *Science* 262, 1065–1069
51. Flynn, D.C., Leu, T. H., Reynolds, A. B., Parsons, J. T. (1993) *Mol Cell Biol* 13, 7892–900
52. Nada, S., Yagi, T., Takeda, H., Tokunaga, T., Nakagawa, H., Ikawa, Y., Okada, M., Aizawa, S. (1993) *Cell* 73, 1125–1135

We claim:

1. An isolated DNA molecule comprising a DNA sequence selected from the group consisting of:
   (a) nucleotides 1–87 of the sequence shown on FIG. 8 (SEQ ID NO: 8);
   (b) DNA sequences complementary to the sequence in (a); and
   (c) DNA sequences which only differ from the sequences in (a) or (b) due to the degeneracy of the genetic code.

2. The DNA molecule of claim 1, which encodes the peptide of FIG. 8 (SEQ ID. NO: 9).

3. The DNA molecule of claim 1, in which the DNA sequence is operably linked to regulatory control sequences.

4. A plasmid comprising the DNA of claim 3.

5. A recombinant cell transformed with the plasmid of claim 4.

6. The DNA molecule of claim 1, comprising the DNA sequence shown on FIG. 8 (SEQ ID NO: 8).

7. An isolated DNA molecule comprising a DNA sequence selected from the group consisting of:
   (a) nucleotides 1–987 of the sequence shown on FIG. 7 (SEQ ID NO: 6);
   (b) DNA sequences complementary to the sequence in (a); and
   (c) DNA sequences which only differ from the sequences in (a) or (b) due to the degeneracy of the genetic code.

8. The DNA molecule of claim 7, which encodes the peptide of FIG. 7 (SEQ ID. NO: 7).

9. The DNA molecule of claim 7, in which the DNA sequence is operably linked to regulatory control sequences.

10. A plasmid comprising the DNA of claim 9.

11. A recombinant cell transformed with the plasmid of claim 10.

12. The DNA molecule of claim 7, comprising the DNA sequence shown on FIG. 7 (SEQ ID NO: 6).

13. An isolated DNA molecule comprising a DNA sequence selected from the group consisting of:
   (a) nucleotides 1–1107 of the sequence shown on FIG. 6 (SEQ ID NO: 4);
   (b) DNA sequences complementary to the sequence in (a); and
   (c) DNA sequences which only differ from the sequences in (a) or (b) due to the degeneracy of the genetic code.

14. The DNA molecule of claim 13, which encodes the peptide of FIG. 6 (SEQ ID. NO: 5).

15. The DNA molecule of claim 13, in which the DNA sequence is operably linked to regulatory control sequences.

16. A plasmid comprising the DNA of claim 15.

17. A recombinant cell transformed with the plasmid of claim 16.

18. The DNA molecule of claim 13, comprising the DNA sequence shown on FIG. 6 (SEQ ID NO: 4).

* * * * *